United States Patent [19]

Abraham et al.

[11] Patent Number: 5,436,337
[45] Date of Patent: Jul. 25, 1995

[54] AMINES TO SENSITIZE MULTIDRUG-RESISTANT CELLS

[75] Inventors: Irene Abraham, Kalamazoo; Jackson B. Hester, Jr., Galesburg, both of Mich.

[73] Assignee: The Upjohn Company, Kalamazoo, Mich.

[21] Appl. No.: 132,515

[22] Filed: Oct. 6, 1993

Related U.S. Application Data

[63] Continuation-in-part of Ser. No. 682,809, Apr. 9, 1991, abandoned.

[51] Int. Cl.⁶ ............................................. C07D 403/02
[52] U.S. Cl. ................................... 544/295; 544/373
[58] Field of Search ................. 544/373, 295; 514/255, 514/273

[56] References Cited

U.S. PATENT DOCUMENTS

| | | | |
|---|---|---|---|
| 4,066,648 | 1/1978 | Oka et al. | 260/268 |
| 4,179,510 | 12/1979 | McCall | 424/267 |
| 4,206,113 | 6/1980 | Dimroth et al. | 260/157 |
| 4,206,123 | 6/1980 | McCall | 549/23 |
| 4,335,126 | 6/1982 | Kleenmann et al. | 514/255 |
| 4,487,774 | 12/1984 | McCall | 424/256 |
| 4,577,021 | 3/1986 | McCall | 544/376 |
| 4,711,960 | 12/1987 | McCall | 544/364 |
| 4,810,701 | 3/1989 | Kurdjumova et al. | 514/181 |
| 4,829,065 | 5/1989 | Pascal et al. | 514/255 |

FOREIGN PATENT DOCUMENTS

87/01706  3/1987  WIPO ........................ C07J 41/00
88/08424  11/1988  WIPO ........................ C07D 401/14

OTHER PUBLICATIONS

Cancer Letters 50, 45–51 (1990).
W. A. King et al., "Tumor–Associated Neurological Dysfunction Prevented by Lazaroids in Rats", pp. 112–115, J. Neurosurg., vol. 74, No. 1, Jan. 1991.

*Primary Examiner*—Shailendra Kumar
*Attorney, Agent, or Firm*—Bruce Stein

[57] ABSTRACT

The sensitizing amines of the present invention, illustrated by the steroidal amines (I)

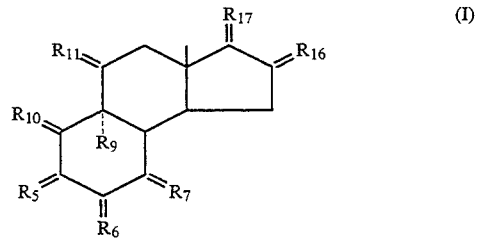

the alkyl amines (II), bicyclic amines (III), bicyclic ethers (IV), tricyclic compounds (V), indoles (VI) and various species are useful in treating individuals who have cancer has become resistant to cancer chemotherapeutic agents and in preventing the resistance from developing or slowing the rate of resistance to the chemotherapeutic agents.

1 Claim, No Drawings

AMINES TO SENSITIZE MULTIDRUG-RESISTANT CELLS

CROSS-REFERENCE TO RELATED APPLICATIONS

The present patent application is a continuation (national phase) application of PCT application PCT/US92/02237, filed 3-27-92 which is a continuation-in-part of U.S. application Ser. No. 07/682,809, filed 4-9-91, now abandoned.

BACKGROUND OF THE INVENTION

1. Field of the Invention

The present invention is a method of sensitizing desensitized cancer cells to various chemotherapeutic agents so as to better treat the cancer.

2. Description of the Related Art

It is known that cancer cells become resistant to some chemotherapeutic agents and are even resistant to many different chemotherapeutic agents. This is a significant impediment to cancer chemotherapeutic treatment.

It would be of great benefit to those who have cancers which can be treated with chemotherapeutic agents to have an agent which will sensitize the resistant cancer cells to the chemotherapeutic agents being used to treat the cancer.

Several classes of compounds which sensitize cancer cells to chemotherapeutic agents are known. One group of compounds are calcium channel blockers or related analogues, some of which no longer act as calcium channel blockers. For example, some synthetic isoprenoids Cancer Research 46, 4453 (1986) and pyridine analogs Int. J. Cancer 45,508 (1990), cause multidrug resistance reversal. Reserpine Biochem. Pharmacol. 30, 2191 (1981), quinidine and cyclosporine and related analogs J. Clin. Invest. 77, 1405 (1986) some without the original bioactivities, also sensitize multidrug resistance cells. Phenothiazines such as the calmodulin inhibitors thioridazine, trifluoperazine and chlorpromazine J. Nat. Cancer Inst. 76, 839 (1986) and Cancer Let. 30, 25 1 (1986) sensitize multidrug resistant cells. Analogs of Vinca alkaloids and anthracyclines such as N-acetyl-daunorubicin Cancer Res. 40, 1077 (1980) will also sensitize multidrug resistant cells, as will steroids J. Biol. Chem. 264, 782 (1989), and Biochem. Biophys. Res. Commun. 158, 1066 (1989)]. Other agents that sensitize multidrug resistant cells include the antibiotic cefoperazone Cancer Research 49, 6901 (1989), tamoxifen Cancer Res. ,,4, 4392 (1984), vitamin A, Br. J. Cancer 56, 267 (1987) and chloroquine Cancer Lett. 30, 251 (1986).

At least two features seem to be of major importance in determining whether a compound can act as a sensitizer. One is lipophilicity Cancer Res. 50, 3997 (1990) and the other is ability to modulate binding on the P-glycoprotein, Advances In Pharmacol., 21,185 (1990). Several of the previously identified sensitizing compounds appear to act by competing for binding to the P-glycoprotein. The mode of action of others that do not compete for binding is unknown.

The steroidal amines (I) are known, see International Publication No. WO87/01706, published Mar. 26, 1987 based on International Patent Application No. PCT/US86/01797.

The alkyl amines (II) and the bicyclic amines (III) are known, see International Publication No. WO88/08424, published Nov. 3, 1988 based on International Patent Application No. PCTAJS88/01212.

The bicyclic ethers (IV) are known, see for example, U.S. Pat. Nos. 4,206,123, 4,577,021, 4,711,960 and 4,487,774. In addition U.S. Pat. Nos. 4,066,648, 4,179,510 and 4,206,113 also disclose bicyclic ethers (IV).

The tricyclic amines (V) am known see U.S. Pat. No. 4,487,774.

Internation Patent Publication WO87/07895 disclosed compounds of the type set forth in ENUMERATED EMBODIMENT 36.

It has been found that various steroidal and non-steroidal amines also sensitize desensitized cancer cells to the common chemotherapeutic agents. These sensitizing compounds are useful in anti-cancer therapy to sensitize cancer cells to be killed by traditional cytotoxic drugs (chemotherapeutic agent). More particularly, 21-[4-2,6-di-1-pyrrolidinyl)-4-pyrimidinyl-1-piperazinyl]-16α-methylpregna-1,4,9(11)-triene-3,20-dione (tirilazad mesylate) sensitizes desensitized cancer cells as well as or better than verapamil, which is a standard sensitizer. Verapamil has the disadvantage of causing cardiac toxicity in humans at doses that are required for in vivo sensitization of cancer cells.

SUMMARY OF INVENTION

Disclosed is a method of treating resistance to cancer chemotherapeutic agents in human cancer patients which comprises administering to that human an effective amount of a sensitizing steroidal amine of formula (I)

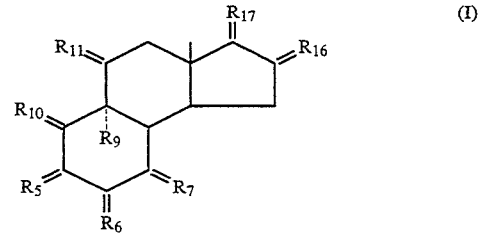

where:

(A-I) $R_6$ is $\alpha\text{-}R_{6\text{-}1}\text{:}\beta\text{-}R_{6\text{-}2}$, $R_{10}$ is $\alpha\text{-}R_{10\text{-}1}\text{:}\beta\text{-}R_{10\text{-}2}$ and $R_7$ is $\alpha\text{-H}\text{:}\beta\text{-H}$, where one of $R_{6\text{-}1}$ and $R_{6\text{-}2}$ is —H, and the other is —H, —F, or $C_1\text{-}C_3$ alkyl, $R_{10\text{-}2}$ is —CH$_3$, $R_{10\text{-}1}$ and $R_5$ taken together are —(CH$_2$)$_2$—C(=R$_{3\text{-}3}$)—CH= or —CH=CH—CO—CH=, where $R_{3\text{-}3}$ is =O or $\alpha\text{-H}\text{:}\beta\text{-OR}_{3\text{-}4}$ or $\alpha\text{-OR}_{3\text{-}4}\text{:}\beta\text{-H}$, where $R_{3\text{-}4}$ is —H, —CO—CH$_3$, —CO—C$_2$H$_5$, —CO—C$_6$H$_5$, —CO—O—CH$_3$ or —CO—O—C$_2$H$_5$;

(A-II) $R_5$ is $\alpha\text{-}R_{5\text{-}3}\text{:}\beta\text{-}R_{5\text{-}4}$, $R_6$ is $\alpha\text{-}R_{6\text{-}3}\text{:}\beta\text{-}R_{6\text{-}4}$, $R_{10}$ is $\alpha\text{-}R_{10\text{-}3}\text{:}\beta\text{-}R_{10\text{-}4}$ and $R_7$ is $\alpha\text{-H}\text{:}\beta\text{-H}$, where one of $R_{6\text{-}3}$ and $R_{6\text{-}4}$ is —H, and the other taken together with one of $R_{5\text{-}3}$ and $R_{5\text{-}4}$ forms a second bond between $C_5$ and $C_6$, $R_{10\text{-}4}$ is —CH$_3$, $R_{10\text{-}3}$ and the other of $R_{5\text{-}3}$ and $R_{5\text{-}4}$ taken together is —(CH$_2$)$_2$—C(H)(OH)—CH$_2$—;

(A-III) $R_{10}$ and $R_5$ taken together are =CH—CH=C(OR$_3$)—CH= where $R_3$ is —H, $C_1\text{-}C_3$ alkyl, —CO—H, $C_2\text{-}C_4$ alkanoyl or benzyl, $R_6$ is $\alpha\text{-}R_{6\text{-}5}\text{:}\beta\text{-}R_{6\text{-}6}$ where one of $R_{6\text{-}5}$ and $R_{6\text{-}6}$ is —H, and the other is —H, —F, or $C_1\text{-}C_3$ alkyl and $R_7$ is $\alpha\text{-H}\text{:}\beta\text{-H}$;

(A-IV) $R_5$ is $\alpha\text{-}R_{5\text{-}7}\text{:}\beta\text{-}R_{5\text{-}8}$, $R_6$ is $\alpha\text{-}R_{6\text{-}7}\text{:}\beta\text{-}R_{6\text{-}8}$, $R_7$ is $\alpha\text{-H}\text{:}\beta\text{-H}$ and $R_{10}$ is $\alpha\text{-}R_{10\text{-}7}\text{:}\beta\text{-}R_{10\text{-}8}$, where one of $R_{5\text{-}7}$ and $R_{5\text{-}8}$ is —H, $R_{10\text{-}7}$ and the other of $R_{5\text{-}7}$ and $R_{5\text{-}8}$ taken together are —(CH$_2$)$_2$—C(=R$_{3\text{-}3}$)—CH$_2$, where $R_{3-3}$ is as defined above, $R_{10-8}$ is —CH$_3$, where one of $R_{6-7}$ and $R_{6-8}$ is —H and the other is —H, —F, or $C_1$-$C_3$ alkyl;

(A-V) $R_6$ is $R_{6-9}$:$R_{6-10}$, $R_7$ is $R_{7-9}$:$R_{7-10}$, $R_{10}$ is s $\alpha$-$R_{10-9}$:$R_{10-10}$, where one of $R_{6-9}$ and $R_{6-10}$ is —H and the other taken together with one of $R_{7-9}$ and $R_{7-10}$ forms a second bond between $C_6$ and $C_7$, and the other of $R_{7-9}$ and $R_{7-10}$ is —H, $R_{10-10}$ is —CH$_3$, $R_{10-9}$ and $R_5$ taken together are —(CH$_2$)$_2$—C(=$R_{3-3}$)—CH= or —CH=CH—CO—CH=, where $R_{3-3}$ is as defined above; where:

(C-I) $R_{11}$ is $\alpha$-$R_{11-1}$:$\beta$-$R_{11-2}$, where one of $R_{11-1}$ and $R_{11-2}$ is taken together with $R_9$ to form a second bond between $C_9$ and $C_{11}$ and the other of $R_{11-1}$ and $R_{11-2}$ is —H;

(C-II) $R_9$ is —Cl and $R_{11}$ is =O or $\alpha$-H:$\beta$-$R_{11-4}$ where $R_{11-4}$ is —Cl or —OH;

(C-III) $R_9$ is —H or —F and $R_{11}$ is =O or $\alpha$-$R_{11-5}$:$\beta$-$R_{1-6}$, where one of $R_{11-5}$ and $R_{11-6}$ is —H, and the other of $R_{11-5}$ and $R_{11-6}$ is —H, —OH or $C_1$-$C_{12}$ alkoxy;

(C-IV) $R_9$ is —H or —F and $R_{11}$ is $\alpha$-O—CO—$R_{11-7}$:$\beta$-H, where $R_{11-7}$ is (A) $C_1$-$C_3$ alkyl,
(B) $C_1$-$C_{12}$ alkoxy,
(C) furanyl,
(D) —NR$_{122}$R$_{123}$, where one of $R_{122}$ and $R_{123}$ is —H, methyl or ethyl and the other is —H, $C_1$-$C_4$ alkyl or phenyl,
(E) —X$_3$-Aryl, where X$_3$ is —O— or a valence bond, where Aryl is phenyl optionally substituted with 1 thru 2 —Cl, —Br, $C_1$-$C_3$ alkoxy, —COOH, —NH$_2$, $C_1$-$C_3$ alkylamino, di($C_1$-$C_3$)alkylamino, where the alkyl groups are the same or different, 1-pyrrolidinyl, 1-piperidinyl, 1-hexamethylenimino, 1-heptamethylenimino, $C_2$-$C_4$ acylamino and —NH—CHO or with 1 —F or —CF$_3$;

where:

(D-I) $R_{16}$ is $R_{16-1}$:$R_{16-2}$ and $R_{17}$ is $R_{17-1}$:$R_{17-2}$, where one of $R_{16-1}$ and $R_{16-2}$ is —H or —CH$_3$ and the other taken together with one of $R_{17-1}$ and $R_{17-2}$ forms a second bond between $C_{16}$ and $C_{17}$, and the other of $R_{17-1}$ and $R_{17-2}$ is —C(=Z)—(CH$_2$)$_n$—NR$_{21-\alpha}$R$_{21-\beta}$, where Z is =O, =CH$_2$ or $R_{17-9}$: —H where $R_{17-9}$ is —H or —CH$_3$, where n is 0 thru 6, where (A) $R_{21-\alpha}$ is
(1) —(CH$_2$)$_m$—NR$_{21-1}$-Heteroaryl, where m is 2, 3 or 4, where $R_{21-1}$ is —H or $C_1$-$C_3$ alkyl, where Heteroaryl is:
(a) pyridin-2- (F-1), 3- (F-2) or 4-yl (F-3) or the N-oxide thereof optionally substituted by 1 or 2 $R_{21-2}$, being the same or different, where $R_{21-2}$ is
(i) —F,
(ii) —Cl,
(iii) —Br,
(iv) $C_1$-$C_5$ alkyl,
(v) —CH$_2$—CH=CH$_2$,
(vi) -Aryl, where Aryl is as defined above,
(vii) —NR$_{21-3}$R$_{21-3}$ where the $R_{21-3}$'s are the same or different and are —H, $C_1$-$C_3$ alkyl or —CH$_2$—CH=CH$_2$,
(viii$\alpha$) *CH$_2$—(CH$_2$)$_q$—CH$_2$—N*—where the atoms marked with an asterisk (*) are bonded to each other resulting in the formation of a ring, where q is 1 thru 5,
(viii$\beta$) *CH$_2$—CH$_2$—(CH$_2$)$_c$—G—(CH$_2$)$_d$—CH$_2$—CH$_2$—N* —where the atoms marked with an asterisk (*) are bonded to each other resulting in the formation of a ring (F-4), where G is —O—, —S—, —SO—, —SO$_2$— or —NHR$_{21-4}$, where $R_{21-4}$ is —H, $C_1$-$C_3$ alkyl or Aryl as defined above, where c and d are the same or different and are 0 thru 2 with the proviso that the total number of ring carbon atoms is 4, 5 or 6,
(ix) 3-pyrrolin- 1-yl, (F-5)
(x) pyrrol-1-yl optionally substituted with $C_1$-$C_3$ alkyl, (F-6)
(xi) piperidin-1-yl optionally substituted with 1 or 2 $C_1$-$C_3$ alkyl, (F-7)
(xii) 1,2,3,6-tetrahydropyridin-1-yl, (F-8)
(xiii) 1-hexamethyleneimino containing a 3- or 4- double bond or 3- and 5- double bonds, (F-9)
(xiv) 1,4-dihydro- 1-pyridinyl substituted in the 4 position by two $C_1$-$C_3$ alkyl being the same or different, (F-10)
(xv) —OH,
(xvi) $C_1$-$C_3$ alkoxy,
(xvii) —NR$_{21-7}$—(CH$_2$)$_e$—Q where Q is 2-pyridinyl where $R_{21-7}$ is —H or $C_1$-$C_3$ alkyl and e is 0 thru 3,
(xviii) pyridin-2-, 3- or 4-yl,
(b) 1,3,5-triazin-2-yl or the N-oxide thereof optionally substituted at the 4- and/or 6- position with $R_{21-2}$ is as defined above, (F-11)
(c) pyrimidin-4-yl or the N-oxide thereof optionally substituted at the 2- and/or 6- position with $R_{21-2}$ is as defined above, (F-12)
(d) pyrimidin-2-yl optionally substituted at 4- and/or 6- position with 1 or 2 $R_{21-2}$ as is defined above, (F-13)
(e) pyrazin-2-yl optionally substituted with 1 or 2 $R_{21-2}$ as is defined above, (F- 14)
(f) imidazol-2-yl optionally substituted in the 1 position with $C_1$-$C_3$ alkyl or -Aryl, where Aryl is as defined above, and further optionally substituted with 1 or 2 $R_{21-2}$ as defined above, (F-15)
(g) 1,2,4-triazol-3-yl optionally substituted in the 1 position with $C_1$-$C_3$ alkyl or -Aryl, where Aryl is as defined above, and further optionally substituted with $R_{21-2}$ as defined above, (F-16)
(h) imidazol-4- or 5-yl optionally substituted in the 1 position with $C_1$-$C_3$ alkyl or -Aryl, where Aryl is as defined above, and further optionally substituted with 1 or 2 $R_{21-2}$ as defined above, (F-17)
(i) benzo[b]thien-2-yl, (F-18)
(j) indol-2-yl, (F-19)
(k) benzo[b]thiazol-2-yl, (F-20)
(l) benzimidazol-2-yl, (F-21)
(m) 4-[2-[4-[2,6-bis(1-pyrrolidinyl)-4-pyrimidinyl]-1-piperazinyl ]ethyl]piperazinyl, (F-22)
(n) 1,2,4-triazol-3-yl optionally substituted at the 5- and/or 6-position with $R_{21-2}$ as is defined above, (F-23)
(2) (1-piperazinyl)-($C_2$-$C_4$)alkyl optionally substituted in the 4-position with -Aryl or -Heteroaryl as defined above, (F-24)
(4) —(CH$_2$)$_m$-X$_4$ where m is as defined above and where X$_4$ is (a) —O—CH$_2$CH$_2$—Y, where Y is C$_1$-C$_3$ alkylamino, di(C$_1$-C$_3$)alkylamino where the alkyl groups are the same or different, C$_3$-C$_6$ alkyleneimino, optionally substituted with 1 or 2 C$_1$-C$_3$ alkyl, (b) —NR$_{21-20}$CH$_2$CH$_2$—Y, where R$_{21-20}$ is —H or C$_1$-C$_3$ alkyl and Y is as defined above, (c) —(CH$_2$)$_g$—N(R$_{21-20}$)-Heteroaryl, where g is 2, 3 or 4, and where R$_{21-20}$ and Heteroaryl are as defined above, (5) —(CH$_2$)$_m$—NR$_{21-22}$R$_{21-23}$, where R$_{21-22}$ is —H or C$_1$-C$_3$ alkyl and R$_{21-23}$ is -Aryl or -Heteroaryl as defined above, or R$_{21-22}$ and R$_{21-23}$ are taken together with the attached nitrogen atom to form a saturated mono-nitrogen C$_3$-C$_6$ heterocyclic ring and where m is as defined above, (6) —(CHCH$_3$)$_b$—(CH$_2$)$_f$R$_{21-24}$, where b is 0 and f is 1 thru 3 or b is one and f is 0 thru 3, where R$_{21-24}$ is phenyl substituted with 1 thru 3 —OH, C$_1$-C$_3$ alkoxy, —NR$_{21-25}$R$_{21-26}$ where R$_{21-25}$ and R$_{21-26}$ are the same or different and are —H, C$_1$-C$_3$ alkyl or are taken together with the attached nitrogen atom to form a C$_4$-C$_7$ cyclicamino ring, (7) —(CH$_2$)$_i$—Heteroaryl, where i is 1 thru 4 and Heteroaryl is as defined above, (8) (1-piperazinyl)acetyl substituted in the 4- position by Heteroaryl where Heteroaryl is as defined above, (F-25)

(9) (1-piperazinyl)carbonylmethyl substituted in the 4- position by -Heteroaryl where Heteroaryl is as defined above, and (F-26)

(B) R$_{21-\beta}$ is (1) —H,
(2) C$_1$-C$_3$ alkyl,
(3) C$_5$-C$_7$ cycloalkyl,
(4) —(CH$_2$)$_m$—NR$_{21-1}$-Heteroaryl, where m, R$_{21-1}$ and Heteroaryl are as defined above,
(5) (1-piperazinyl)-(C$_2$-C$_4$)alkyl optionally substituted in the 4- position with -Aryl or -Heteroaryl as defined above, (F-24)
(6) —(CH$_2$)$_m$—X$_4$, where m and X$_4$ are as defined above,
(7) —(CH$_2$)$_m$—NR$_{21-22}$R$_{21-23}$, where m, R$_{21-22}$ and R$_{21-23}$ are as defined above,
(8) —(CHCH$_3$)$_b$—(CH$_2$)$_f$—R$_{21-24}$, where b, f and R$_{21-24}$ are as defined above, (C) R$_{21-\alpha}$ and R$_{21-\beta}$ are taken together with the attached nitrogen atom to form a heterocyclic ring selected from the group consisting of (1) 2-(carboxy)-1-pyrrolidinyl optionally as the C$_1$-C$_3$ alkyl ester or as a pharmaceutically acceptable salt, (F-27)
(2) 2-(carboxy)-1-piperidinyl optionally as the C$_1$-C$_3$ alkyl ester or as a pharmaceutically acceptable salt, (F-28)
(3) 2-(carboxy)-1-hexamethyleneimino optionally as the C$_1$-C$_3$ alkyl ester or as a pharmaceutically acceptable salt, (F-29)
(4) 2-(carboxy)-1-heptamethyleneimino optionally as the C$_1$-C$_3$ alkyl ester or as a pharmaceutically acceptable salt, (F-30)
(5) 1-piperazinyl substituted in the 4- position with R$_{21-28}$ —CO—(CH$_2$)$_j$— where R$_{21-28}$ is -Aryl, —NR$_{21-29}$Aryl and 2-furanyl, where R$_{21-29}$ is —H or C$_1$-C$_3$ alkyl, where j is 0 thru 3 and Aryl is as defined above, (F-31)

(6) 1-piperazinyl substituted in the 4- position with Heteroaryl-(CH$_2$)$_j$—, where Heteroaryl and j are as defined above, (F-32)
(7) 1-piperazinyl substituted in the 4- position with Aryl-(CH$_2$)$_j$—, where Aryl and j are as defined above, (F-33)
(8) 4-hydroxy-1-piperidinyl substituted in the 4- position with Aryl as defined above, (F-34)
(9) 1-piperazinyl substituted in the 4- position with Heteroaryl—NR$_{21-29}$-CO—(CH$_2$)$_i$—, where Heteroaryl, R$_{21-29}$ and i are as defined above; (F-35)

(D-II) R$_{16}$ is $\alpha$-R$_{16-3}$:$\beta$-R$_{16-4}$ where one of R$_{16-3}$ and R$_{16-4}$ is —H and the other is —H, —F, —CH$_3$ or —OH, and R$_{17}$ is =CH—(CH$_2$)$_p$NR$_{21-\alpha}$R$_{21-\alpha}$, where p is 1 or 2, where R$_{21-\alpha}$ and R$_{21-\beta}$ are as defined above;

(D-III) R$_{16}$ is $\alpha$-R$_{16-5}$:$\beta$-R$_{16-6}$ and R$_{17}$ is $\alpha$-R$_{17-5}$:$\beta$-R$_{17-6}$, where R$_{16-5}$ is —H, —OH, —F or —CH$_3$ and R$_{16-6}$ is —H, —OH, —F, or —CH$_3$, with the proviso that at least one of R$_{16-5}$ and R$_{16-6}$ is —H, where R$_{17-5}$ is —H, —OH, —CH$_3$, —CH$_2$CH$_3$, C$_2$-C$_7$ alkanoyloxy or —O—CO-Aryl, where Aryl is as defined above, and where R$_{17-6}$ is —C(=Z)—(CH$_2$)$_n$—NR$_{21-\alpha}$R$_{21-\beta}$, where Z, n, R$_{21-\alpha}$ and R$_{21-\beta}$ are as defined above;

(D-IV) the 16,17-acetonide of a compound where R$_{16-5}$ is —OH, R$_{16-6}$ is —H, R$_{17-5}$ is —OH and R$_{17-6}$ is —C(=Z)—(CH$_2$)$_n$—NR$_{21-\alpha}$ R$_{21-\beta}$, where Z, n, R$_{21-\alpha}$ and R$_{21-\beta}$ are as defined above;

with the following overall provisos that:
(I) one of R$_{16-1}$ or R$_{16-2}$ is taken together with one of R$_{17-1}$ or R$_{17-2}$ to form a second bond between C$_{16}$ and C$_{17}$, only when R$_{10}$ is $\alpha$-R$_{10-1}$:$\beta$-R$_{10-2}$, $\alpha$-R$_{10-3}$:$\beta$-R$_{10-4}$, $\alpha$-R$_{10-7}$:$\beta$-R$_{10-8}$ or $\alpha$-R$_{10-9}$:$\beta$-R$_{10-10}$, (II) R$_{17}$ is =CH-(CH$_2$)$_p$—NR$_{21-\alpha}$R$_{21-\beta}$, only when R$_{10}$ is $\alpha$-R$_{10-1}$:$\beta$-R$_{10-2}$, $\alpha$-R$_{10-3}$:$\beta$-R$_{10-4}$, $\alpha$-R$_{10-7}$:$\beta$-R$_{10-8}$ or $\alpha$-R$_{10-9}$:$\beta$-R$_{10-10}$, (III) R$_5$ and R$_{10}$ taken together are =CH—CH=C(OR$_3$)—CH=, only when R$_{17}$ is $\alpha$-R$_{17-5}$:$\beta$-R$_{17-6}$ or the 16,17-acetonide of a compound where R$_{16}$ is $\alpha$-OH:$\beta$-H and R$_{17}$ is $\alpha$-OH: $\beta$—C(=Z)—(CH$_2$)$_n$—NR$_{21-\alpha}$R$_{21-\beta}$, and (IV) R$_5$ is $\alpha$-R$_{5-7}$:$\beta$-R$_{5-8}$, only when R$_{17}$ is $\alpha$-R$_{17-5}$:$\beta$-R$_{17-6}$ or $\alpha$-OH:$\beta$—C-(=Z)—(CH$_2$)$_n$—NR$_{21-\alpha}$R$_{21-\beta}$, or the 16, 17-acetonide thereof; and pharmaceutically acceptable salts thereof.

Also disclosed is a method of treating resistance to cancer chemotherapeutic agents in human cancer patients which comprises administering to that human an effective amount of a sensitizing alkyl amine of formula (II)

$$X_2-(CH_2)_{n2}-NR_{21-\alpha}R_{21-\beta} \qquad (II)$$

where:
n$_2$ is 3-14;
X$_2$ is
—H,
—OH,
—O—CO—(C$_1$-C$_4$ alkyl),
—O—CO—H,
—O—CO—O—(C$_1$-C$_4$ alkyl),
(C$_1$-C$_4$) alkoxycarbonyl,
—O—CO-Aryl where Aryl is —$\phi$ optionally substituted with 1 thru 3 of the following which may be the same or different:
—OH,
—OCH$_3$, —F, —Cl, —Br, —CF$_3$,
—C$_1$-C$_3$ alkyl, and
—CO—R$_5$ where R$_5$ is
—OH,
—NH$_2$,
—NHR$_6$ where R$_6$ is
φ,
C$_1$-C$_3$ alkyl and
—N(R$_{14}$)(R$_{15}$) where R$_{14}$ and R$_{15}$ are the same or different and are C$_1$-C$_3$ alkyl,
—O—Aryl, where Aryl is as defined above,
—CH(OH)Aryl, where Aryl is as defined above,
Aryl, where aryl is as defined above;
(A) R$_{21-\alpha}$ is
(1) —(CH$_2$)$_m$—NR$_{21-1}$-Heteroaryl, where m is 2, 3 or 4, where R$_{21-1}$ is —H or C$_1$-C$_3$ alkyl, where Heteroaryl is:
  (a) pyridin-2- (F-1), 3- (F-2) or 4-yl (F-3) or the N-oxide thereof optionally substituted by 1 or 2 R$_{21-2}$, being the same or different, where R$_{21-2}$ is
    (i) —F,
    (ii) —Cl,
    (iii) —Br,
    (iv) C$_1$-C$_5$ alkyl,
    (v) —CH$_2$-CH=CH$_2$,
    (vi) -Aryl, where Aryl is phenyl optionally substituted with 1 through 2 —F, —Cl, —Br, C$_1$-C$_3$ alkoxy, —COOH, —NH$_2$, C$_1$-C$_3$ alkylamino, di(C$_1$-C$_3$)alkylamino, where the alkyl groups are the same or different, 1-pyrrolidinyl, 1-piperidinyl, 1-hexamethylenimino, 1-heptamethylenimino, C$_2$-C$_4$ acylamino and —NH—CHO or with 1 —F or —CF$_3$;
    (vii) —NR$_{21-3}$R$_{21-3}$ where the R$_{21-3}$s are the same or different and are —H, C$_1$-C$_3$ alkyl or —CH$_2$-CH=CH$_2$,
    (viiiα) * CH$_2$—(CH$_2$)$_q$—CH$_2$—N*— where the atoms marked with an asterisk (*) are bonded to each other resulting in the formation of a ring, where q is 1 through 5,
    (viiiβ) * CH$_2$—(CH$_2$)$_c$—G—(CH$_2$)$_d$—CH$_2$—N*— where the atoms marked with an asterisk (*) are bonded to each other resulting in the formation of a ring (F4), where G is —O—, —S—, —SO—, —SO$_2$— or —NR$_{2-14}$—, where R$_{21-4}$ is —H, C$_1$-C$_3$ alkyl, or Aryl as defined above, where c and d are the same or different and are 0 through 2 with the proviso that the total number of ring carbon atoms is 4, 5 or 6,
    (ix) 3-pyrrolin-1-yl, (F-5)
    (x) pyrrol-1-yl optionally substituted with C$_1$-C$_3$ alkyl, (F-6)
    (xi) piperidin-1-yl optionally substituted with 1 or 2 C$_1$-C$_3$ alkyl, (F-7)
    (xii) 1,2,3,6-tetrahydropyridin- 1-yl, (F-8)
    (xiii) 1-hexamethyleneimino containing a 3- or 4- double bond or 3- and 5- double bonds, (F-9)
    (xiv) 1,4-dihydro-1-pyridinyl substituted in the 4 position by two C$_1$-C$_3$ alkyl being the same or different, (F-10)
    (xv) —OH,
    (xvi) C$_1$-C$_3$ alkoxy,
    (xvii) —NR$_{21-7}$—(CH$_2$)$_e$—Q where Q is 2-pyridinyl where R$_{21-7}$ is —H or C$_1$-C$_3$ alkyl and e is 0 through 3,
    (xviii) pyridin-3- or 4-yl,
    (xix) —CF$_3$,
    (xx) —CCl$_3$,
    (xxi) —SCH$_3$,
  (b) 1,3,5-triazin-2-yl or the N-oxide thereof optionally substituted at the 4- and/or 6- position with R$_{21-2}$ is as defined above, (F-11)
  (c) pyrimidin-4-yl or the N-oxide thereof optionally substituted at the 2- and/or 6-, and 5- and/or 6- position with R$_{21-2}$ is as defined above, (F-12)
  (d) pyrimidin-2-yl optionally substituted at 4- and/or 6- position with 1 or 2 R$_{21-2}$ as is defined above, (F-13)
  (e) pyrazin-2-yl optionally substituted with 1 or 2 R$_{21-2}$ as is defined above, (F-14)
  (f) imidazol-2-yl optionally substituted in the 1 position with C$_1$-C$_3$ alkyl or -Aryl, where Aryl is as defined above, and further optionally substituted with 1 or 2 R$_{21-2}$ as defined above, (F-15)
  (g) 1,3,4-triazol-2-yl optionally substituted in the 1 position with C$_1$-C$_3$ alkyl or -Aryl, where Aryl is as defined above, and further optionally substituted with R$_{21-2}$ as defined above, (F- 16)
  (h) imidazol-4- or 5-yl optionally substituted in the 1 position with C$_1$C$_3$ alkyl or -Aryl, where Aryl is as defined above, and further optionally substituted with 1 or 2 R$_{21-2}$ as defined above, (F-17)
  (i) benzo[b]thien-2-yl, (F-18)
  (j) indol-2-yl, (F-19)
  (k) benzo[b]thiazol-2-yl, (F-20)
  (l) benzimidazol-2-yl, (F-21)
  (m) 4-[2-[4-[2,6-bis(1-pyrrolidinyl)-4-pyrimidinyl]-1-piperazinyl]ethyl], (F-22)
  (n) 1,2,4-triazin-3-yl optionally substituted at the 5- and/or 6- position with R$_{M-2}$ as is defined above, (F-23)
(2) —(CH$_2$)$_{2-4}$—(1-piperazinyl) optionally substituted in the 4- position with -Aryl or -Heteroaryl as defined above, (F-24)
(3) -Heteroaryl, as defined above,
(4) —(CH$_2$)$_m$—X$_4$ where m is as defined above and where X$_4$ is
  (a) —O—CH$_2$CH$_2$—Y, where Y is C$_1$-C$_3$ alkylamino, di(C$_1$-C$_3$)alkylamino where the alkyl groups are the same or different, C$_3$-C$_6$ alkyleneimino, optionally substituted with 1 or 2 C$_1$-C$_3$ alkyl,
  (b) —NR$_{21-5}$CH$_2$CH$_2$—Y, where R$_{21-5}$ is —H or C$_1$-C$_3$ alkyl and Y is as defined above,
  (c) —(CH$_2$)$_g$—N(R$_{21-5}$)-Heteroaryl, where g is 2, 3 or 4, and where R$_{21-5}$ and Heteroaryl are as defined above,
(5) —(CH$_2$)$_m$—NR$_{21-22}$R$_{21-23}$, where R$_{21-22}$ is —H or C$_1$-C$_3$ alkyl and R$_{21-23}$ is -Aryl or -Heteroaryl as defined above, or R$_{21-22}$ and R$_{21-23}$ are taken together with the attached nitrogen atom to form a saturated mono-nitrogen C$_3$-C$_6$ heterocyclic ring and where m is as defined above,
(6) —(CHCH$_3$)$_b$—(CH$_2$)$_f$—Aryl where b is 0 and f is 1 through 4 or b is 1 and f is 0 through 3, where Aryl is as defined above,
(7) —(CH$_2$)$_i$—Heteroaryl, where i is 1 through 4 and Heteroaryl is as defined above,
(8) (1-piperazinyl)acetyl substituted in the 4- position by Heteroaryl where Heteroaryl is as defined above, (F-25)
(9) (1-piperazinyl)carbonylmethyl substituted in the 4- position by -Heteroaryl where Heteroaryl is as defined above, (F-26)
(B) R$_{21-\beta}$ is (1) —H,
(2) $C_1$-$C_3$ alkyl,
(3) $C_5$-$C_7$ cycloalkyl,
(4) —$(CH_2)_m$—$NR_{21-1}$-Heteroaryl, where m, $R_{21-1}$ and Heteroaryl are as defined above,
(5) (1-piperazinyl)-($C_2$-$C_4$)alkyl optionally substituted in the 4- position with -Aryl or-Heteroaryl as defined above, (F-24)
(6) —$(CH_2)_m$—$X_4$, where m and $X_4$ are as defined above,
(7) —$(CH_2)_m$—$NR_{21-22}R_{21-23}$, where m, $R_{21-22}$ and $R_{21-23}$ are as defined above,
(8) —$(CHCH_3)_b$—$(CH_2)_f$—$R_{21-24}$, where $R_{21-24}$ is phenyl substituted with 1 thru 3 —OH, $C_1$-$C_3$ alkoxy, —$NR_{21-25}R_{21-26}$ where $R_{21-25}$ and $R_{21-26}$ are the same or different and are —H, $C_1$-$C_3$ alkyl or are taken together with the attached nitrogen atom to form a $C_4$-$C_7$ cyclicamino ring and where b and f are as defined above,
(9) 2-pyridinylmethyl,
(C) $R_{21-\alpha}$ and $R_{21-\beta}$ are taken together with the attached nitrogen atom to form a heterocyclic ring selected from the group consisting of
(1) 2-(carboxy)-1-pyrrolidinyl optionally as the $C_1$-$C_3$ alkyl ester or as a pharmaceutically acceptable salt, (F-27)
(2) 2-(carboxy)-1-piperidinyl optionally as the $C_1$-$C_3$ alkyl ester or as a pharmaceutically acceptable salt, (F-28)
(3) 2-(carboxy)-1-hexamethyleneimino optionally as the $C_1$-$C_3$ alkyl ester or as a pharmaceutically acceptable salt, (F-29)
(4) 2-(carboxy)-1-heptanethyleneimino optionally as the $C_1$-$C_3$ alkyl ester or as a pharmaceutically acceptable salt, (F-30)
(5) 1-piperazinyl optionally substituted in the 4- position with $R_{21-28}$-$CO(CH_2)_j$— where $R_{21-28}$ is -Aryl, -Heteroaryl, —$NR_{21-29}$Heteroaryl and 2-furanyl, where $R_{21-29}$ is —H or $C_1$-$C_3$ alkyl, where j is 0 through 3, and Aryl and Heteroaryl are as defined above, (F-31)
(6) 1-piperazinyl substituted in the 4- position with Heteroaryl-$(CH_2)_j$—, where Heteroaryl and j are as defined above, (F-32)
(7) 1-piperazinyl substituted in the 4- position with Aryl-$(CH_2)_j$—, where Aryl and j are as defined above, (F-33)
(8) 4-hydroxy-1-piperidinyl substituted in the 4- position with Aryl as defined above, (F-34)
(9) 1-piperazinyl substituted in the 4- position with Heteroaryl—$NR_{21-29}$—CO-$(CH_2)_i$—, where Heteroaryl, $R_{21-29}$ and i are as defined above; (F-35)
(10) 1-piperazinyl substituted in the 4- position with —$(CH_2)_j$—C*=C(2-pyridinyl)—N=N—C(2-pyridinyl)=C*H, where * and j are as defined above, (F-36)
(11)-piperazinyl substituted in the 4- position with —$(CH_2)_i$—[4-[2,6-bis(1-pyrrolidinyl)-4-pyrimidinyl]-1-piperazine](F-37) and pharmaceutically acceptable salts thereof.

Further disclosed is a method of treating resistance to cancer chemotherapeutic agents in human cancer patients which comprises administering to that human an effective amount of a sensitizing bicyclic amine of formula (III)

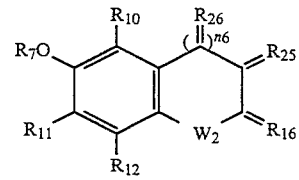

where:
$W_2$ is —O—, —S—, —$NR_{54}$— where $R_{54}$ is —H or $C_1$-$C_3$ alkyl,
$n_6$ is 0, 1 or 2,
$R_7$ is —H, $C_1$-$C_4$ alkyl, —CO—($C_1$-$C_4$ alkyl), —CO—$\phi$ or -prodrug where prodrug is —$PO_2$—$O^-$ cation$^+$ where cation$^+$ is sodium, potassium or trialkylammonium where alkyl is $C_1$-$C_3$,
—CO—$CH_2$—CO—NH—$CH_2$—$SO_2$—O cation$^+$ where cation$^+$ is as defined above,
—CO—$(CH_2)_{n21}$—$R_{51}$ where n21 is 1–7 and $R_{51}$ is —COO$^-$$NR_{51-1}R_{51-2}$ where $R_{51-1}$ and $R_{51-2}$ are the same or different and are —H or $C_1$-$C_3$ alkyl, —N$^+$$R_{51-1}R_{51-2}R_{51-3}$ halide where $R_{51-1}R_{51-2}R_{51-3}$ are the same or different and are —H or $C_1$-$C_3$ alkyl, and where halide is —Cl or —Br,
—CO—CH=CH—CO-O cation$^+$ where cation$^+$ is as defined above,
—CO—N*—CH=CH—N=C*H where the atoms marked with an asterisk (*) are bonded to each other resulting in the formation of a ring,
—CO—C*=C[$(CH_2)$n22—$NH_2$]—CH=-CH—CH=C*H where n22 is 1 or 2 and where the atoms marked with an asterisk (*) are bonded to each other resulting in the formation of a ring,
—CO—C*=CH—CH=C(—$NR_{52}$)—CH=C*H where $R_{52}$ is —H or $C_1$-$C_3$ alkyl and where the atoms marked with an asterisk (*) are bonded to each other resulting in the formation of a ring,
—CO-$(CH_2)$n21 -CO-O-[$C_6H$ 1206 sugars],
—CO-O—CH($CH_2$-O—CO-$R_{53}$)$_2$ where the $R_{53}$'s are the stone or different and are $C_1$-$C_{18}$,
—CO-$(CH_2)$6-CO—N($CH_3$)—$CH_2$-$CH_2$-$SO_3$'cation$^+$ where cation$^+$ is as defined above,
—$CH_2$-O—CO-$(CH_2)_{n21}$—$NR_{51-1}R_{51-2}$ where n21, $R_{51}1$ and $R_{51-2}$ are as defined above,
—CO—NH—$C_6H_4$-$R_{55}$ where $R_{55}$ is —H or $C_1$-$C_3$ alkyl, —$NO_2$, —$NR_{51-1}R_{51-2}$ where
$R_{51-1}$ and $R_{51-2}$ are as defined above and
$R_{10}$ is —H or —$CH_3$,
$R_{11}$ is —H or —$CH_3$,
$R_{12}$ is —H or —$CH_3$,
(18-1) $R_{16}$ is $\alpha$-$R_{16-1}$:$\beta$—$R_{16-2}$ where one of $R_{16-1}$ and $R_{16-2}$ is —H, —$CH_3$, —$CH_2CH_3$ or -$\phi$ and the other is -$X_3$—$NR_{21-\alpha}R_{21-\beta}$ where $X_3$ is —CO—, —$(CH_2)_{n16}$—CO— where $n_{16}$ is 1 or 2, -$(CH_2)_{n3}$— where $n_3$ is 1-6, or —CO—O—$(CH_2)_{n15}$— where $n_{15}$ is 2-6, $R_{25}$ and $R_{26}$ are —H:—H;
(A) $R_{21-\alpha}$ is
(1) —$(CH_2)$m—$NR_{21-1}$—Heteroaryl, where m is 2, 3 or 4, where $R_{21-1}$ is —H or $C_1$-$C_3$ alkyl, where Heteroaryl is:
(a) pyridin-2-(F-1), 3-(F-2) or 4-yl (F-3) or the N-oxide thereof optionally substituted by 1 or 2 $R_{21-2}$, being the same or different, where $R_{21-2}$ is
(i) —F,
(ii) —Cl,
(iii) —Br,
(iv) $C_1$-$C_5$ alkyl, (v) —$CH_2$-CH=$CH_2$, (vi) -Aryl, where Aryl is phenyl optionally substituted with 1 thru 2 —F, —Cl, —Br, $C_1$–$C_3$ alkoxy, —COOH, —$NH_2$, $C_1$-$C_3$ alkylamino, di($C_1$-$C_3$)alkylamino, where the alkyl groups are the same or different, 1-pyrrolidinyl, 1-piperidinyl, 1-hexamethylenimino, 1-heptamethylenimino, $C_2$-$C_4$ acylamino, —NH—CHO, with 1 —F or —$CF_3$ or with 3,4-methylenedioxy and 3,4-ethylenedioxy;

(vii) —$NR_{21-3}R_{21-3}$ where the $R_{21-3}$'s are the same or different and are —H, $C_1$-$C_3$ alkyl or —$CH_2$-CH=$CH_2$, (viiiα) * $CH_2$-$(CH_2)_q$—$CH_2$—N*— where the atoms marked with an asterisk (*) are bonded to each other resulting in the formation of a ring, where q is 1 thru 5, (viiiβ) * $CH_2$-$(CH_2)_c$-G-$(CH_2)_d$—$CH_2$—N*— where the atoms marked with an asterisk (*) are bonded to each other resulting in the formation of a ring (F-4), where G is —O—, —S—, —SO—, —$SO_2$ or —$NR_{21-4}$, where $R_{21-4}$ is —H, $C_1$-$C_3$ alkyl, or Aryl as defined above, where c and d are the same or different and are 0 thru 2 with the proviso that the total number of ring carbon atoms is 4, 5 or 6, (ix) 3-pyrrolin-1-yl, (F-5)

(x) pyrrol-1-yl optionally substituted with $C_1$–$C_3$ alkyl, (F-6)

(xi) piperidin-1-yl optionally substituted with 1 or 2 $C_1$-$C_3$ alkyl, (F-7)

(xii) 1,2,3,6-tetrahydropyridin- 1 -yl, (F-8)

(xiii) 1-hexamethyleneimino containing a 3- or 4- double bond or 3- and 5- double bonds, (F-9)

(xiv) 1,4-dihydro- 1-pyridinyl substituted in the 4 position by two $C_1$-$C_3$ alkyl being the same or different, (F- 10)

(xv) —OH, (xvi) $C_1$-$C_3$ alkoxy, (xvii) —$NR_{21-7}$-$(CH_2)_e$—Q where Q is 2-pyridinyl where $R_{21-7}$ is —H or $C_1$-$C_3$ alkyl and e is 0 thru 3, (xviii) pyridin-2-, 3- or 4-yl, (xix) —$CF_3$, (xx) —$CCl_3$, (xxi) —$SCH_3$, (b) 1,3,5-triazin-2-yl or the N-oxide thereof optionally substituted at the 4- and/or 6- position with $R_{21-2}$ is as defined above, (F-11)

(c) pyrimidin-4-yl or the N-oxide thereof optionally substituted at the 2- and/or 6-, and 5- and/or 6- position with $R_{21-2}$ is as defined above, (F-12)

(d) pyrimidin-2-yl optionally substituted at 4- and/or 6- position with 1 or 2 $R_{21,2}$ as is defined above, (F-13)

(e) pyrazin-2-yl optionally substituted with 1 or 2 $R_{21-2}$ as is defined above, (F- 14)

(f) imidaz-2-yl optionally substituted in the 1 position with $C_1$-$C_3$ alkyl or -Aryl, where Aryl is as defined above, and further optionally substituted with 1 or 2 $R_{21-2}$ as defined above, (F-15)

(g) 1,3,4-triazol-2-yl optionally substituted in the 1 position with $C_1$-$C_3$ alkyl or -Aryl, where Aryl is as defined above, and further optionally substituted with $R_{21-2}$ as defined above, (F- 16)

(h) imidazol-4- or 5-yl optionally substituted in the 1 position with $C_1$-$C_3$ alkyl or -Aryl, where Aryl is as defined above, and further optionally substituted with 1 or 2 $R_{21-2}$ as defined above, (F-17)

(i) benzo[b]thien-2-yl, (F- 18)

(j) indol-2-yl, (F-19)

(k) benzo[b]thiazol-2-yl, (F-20)

(l) benzimidazol-2-yl, (F-21)

(m) 4-[2-[4-[2,6-bis(1-pyrrolidinyl)-4-pyrimidinyl]-1-piperazinyl]ethyl], (F-22)

(n) 1,2,4-triazin-3-yl optionally substituted at the 5- and/or 6- position with $R_{21-2}$ as is defined above, (F-23)

(2) —$(CH_2)_2$,4-(1-piperazinyl) optionally substituted in the 4- position with -Aryl or —Heteroaryl as defined above, (F-24)

(3) —Heteroaryl, as defined above, (4) —$(CH_2)_m$—$X_4$ where m is as defined above and where $X_4$ is (a) —O—$CH_2CH_2$—Y, where Y is $C_1$-$C_3$ alkylamino, di($C_1$-$C_3$)alkylamino where the alkyl groups are the same or different, $C_3$-$C_6$ alkyleneimino, optionally substituted with 1 or 2 $C_1$-$C_3$ alkyl, (b) —$NR_{21-20}CH_2CH_2$—Y, where $R_{21,20}$ is —H or $C_1$-$C_3$ alkyl and Y is as defined above, (c) —$(CH_2)_g$—N($R_{21-20}$)-Heteroaryl, where g is 2, 3 or 4, and where $R_{21-20}$ and Heteroaryl are as defined above, (5) —$(CH_2)_m$—$NR_{21,22}R_{21-23}$, where $R_{21-22}$ is —H or $C_1$-$C_3$ alkyl and $R_{21-23}$ is -Aryl or —Heteroaryl as defined above, or $R_{21-22}$ and $R_{21-23}$ are taken together with the attached nitrogen atom to form a saturated mono-nitrogen $C_3$-$C_6$ heterocyclic and where m is as defined above, (6) —$(CHCH_3)_b$—$(CH_2)_f$-Aryl where b is 0 and f is 1 thru 4 or b is and f is 0 thru 3, where Aryl is defined above, (7) —$(CH_2)_i$-Heteroaryl, where i is 1 thru 4 and Heteroaryl is defined above, (8) (1-piperazinyl)acetyl substituted in the 4- position by Heteroaryl where Heteroaryl is as defined above, (F-25)

(9) (1-piperazinyl)carbonylmethyl substituted in the 4- position by -Heteroaryl where Heteroaryl is as defined above, and (F-26)

(B) $R_{21-β}$ is (1) —H, (2) $C_1$-$C_3$ alkyl, (3) $C_5$-cycloalkyl, (4) -$(CH_2)_m$—$NR_{21-1}$-Heteroaryl, where m, $R_{21-1}$ d Heteroaryl are as defined above, (5) (1-piperazinyl)-($C_2$-$C_4$)alkyl optionally substituted in the 4- position with -Aryl or —Heteroaryl as defined above, (F-24)

(6) —$(CH_2)_m$—$X_4$, where m and $X_4$ are as defined above, (7) —$(CH_2)_m$—$NR_{21-22}R_{21-23}$, where m, $R_{21-22}$ and $R_{21-23}$ are as defined above, (8) —$(CHCH_3)_b$—$(CH_2)_f$—$R_{21-24}$, where $R_{21-24}$ is phenyl substituted with 1 thru 3 —OH, $C_1$-$C_3$ alkoxy, —$NR_{21-25}R_{21-26}$ where $R_{21,25}$ and $R_{21-26}$ are the same or different and are —H, $C_1$-$C_3$ alkyl or are taken together with the attached nitrogen atom to form a $C_4$-$C_7$ cyclicamino ring and where b and f are as defined above, (9) 2-pyridinylmethyl,

(10) 2-phenylethyl, (C) $R_{21-\alpha}$ and $R_{21-1}$ are taken together with the attached nitrogen atom to form a heterocyclic ring selected from the group consisting of (1) 2-(carboxy)-1-pyrrolidinyl optionally as the $C_1$-$C_3$ alkyl ester or as a pharmaceutically acceptable salt, (F-27)

(2) 2-(carboxy)-1-piperidinyl optionally as the $C_1$-$C_3$ alkyl ester or as a pharmaceutically acceptable salt, (F-28)

(3) 2-(carboxy)-1-hexamethyleneimino optionally as the $C_1$-$C_3$ alkyl ester or as a pharmaceutically acceptable salt, (F-29)

(4) 2-(carboxy)-1-heptamethyleneimino optionally as the $C_1$-$C_3$ alkyl ester or as a pharmaceutically acceptable salt, (F-30)

(5) 1-piperazinyl optionally substituted in the 4- position with $R_{21-28}$—CO— $(CH_2)_j$— where $R_{21-28}$ is -Aryl, Heteroaryl, —$NR_{21-29}$Heteroaryl and 2-furanyl, where $R_{21-29}$ is —H or $C_1$-$C_3$ alkyl, where j is 0 thru 3, and Aryl and Heteroaryl are as defined above, (F-31)

(6) 1-piperazinyl substituted in the 4-position with Heteroaryl$(CH_2)_j$— where Heteroaryl and j are as defined above (F-32)

(7) 1-piperazinyl substituted in the 4-position with Aryl-$(CH_2)_j$—, where Aryl and j are as defined above, (F-33)

(8) 4-hydroxy-1-piperidinyl substituted in the 4- position with Aryl as defined above, (F-34)

(9) 1-piperazinyl substituted in the 4- position with Heteroaryl—$NR_{21-29}$—CO—$(CH_2)_i$—, where Heteroaryl, $R_{21-29}$ and i are as defined above; (F-35)

(10) 1-piperazinyl substituted in the 4- position with —$(CH_2)_j$—C*=C(2-pyridinyl)—N=N—C(2-pyridinyl)=C*H, where * and j are as defined above, (F-36)

(11) 1-piperazinyl substituted in the 4- position with -$(CH_2)$i-[4-[2,6-bis(1-pyrrolidinyl)-4-pyrimidinyl]-1-piperazine] where i is as defined above, (F-37)

(12) 1-piperazinyl substituted in the 4- position with $C_1$-$C_3$ alkyl optionally substituted with 1 or 2 Aryl;

(18-2) $n_6$ is 0, $R_{16}$ is $R_{16-3}$:$R_{16-4}$ and $R_{25}$ is $R_{25-3}$: $R_{25-4}$ where one of $R_{16-3}$ and $R_{16-4}$ is taken together with one of $R_{25-3}$ and $R_{25-4}$ to form a second bond between the carbon atoms to which $R_{16}$ and $R_{25}$ are attached and the other of $R_{16-3}$ and $R_{16-4}$ is —$X_3$—$NR_{21-\alpha}R_{21-\beta}$ where $X_3$, $R_{21-\alpha}$ and $R_{21-1}$ are as defined above and the other of $R_{25-3}$ and $R_{25-4}$ is —H, (18-3) $n_6$ is 1, $R_{25}$ is $R_{25-5}$ and $R_{25-6}$ and $R_{26}$ is $R_{26-5}$ and $R_{26-6}$ where one of $R_{25-5}$ and $R_{25-6}$ and one of $R_{26}$ is $R_{26-5}$ and $R_{26-6}$ are taken together to form a second bond between the carbon atoms to which $R_{25}$ and $R_{26}$ are attached and the other of $R_{25.5}$ and $R_{25-6}$ and $R_{26-5}$ and $R_{26-6}$ are —H, and pharmaceutically acceptable salts thereof.

Additionally disclosed is a method of treating resistance to cancer chemotherapeutic agents in human cancer patients which comprises administering to that human an effective amount of a sensitizing bicyclic ether of formula (IV)

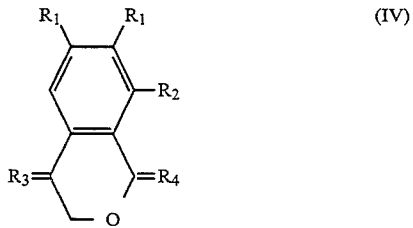

where $R_1$ is —H or —$OR_{1-1}$ where $R_{1-1}$ is $C_1$-$C_3$ alkyl and where $R_2$ is —H or —$OR_{2-1}$ where $R_{2-1}$ is $C_1$-$C_3$ alkyl with the proviso that $R_2$ is not —H only when $R_1$ is —H, $R_3$ is $\alpha$-$R_{3-1}$:$\beta$-$R_{3-2}$ where $R_{3-1}$ and $R_{3-2}$ are the same or different and are —H or —$CH_3$ with the proviso that $R_{3-2}$ is not —$CH_3$ unless $R_{3-1}$ is —$CH_3$, n is 1, 2 or 3, $R_4$ is $R_{4-1}$:$R_{4-2}$ where $R_{4-1}$ is —H, —$CH_3$, —$CH_2CH_3$, 4-fluorophenyl, 4-chlorophenyl, $R_{4-2}$ is —$(CH_2)_n$—$R_{4-3}$ where n is 1, 2 or 3 and where $R_{4-3}$ is —Cl, 1-piperazinyl optionally substituted in the 4-position with a member selected from the group consisting of —$\phi$ optionally substituted with 1 -$CF_3$, —Cl, —F, —$CH_3$, —$CH_2CH_3$, 2-pyridinyl optionally substituted in the 6-position with —$NR_{4-4}R_{4-5}$ where $R_{4-4}$ and $R_{4-5}$ are the same or different and are —H, $C_1$-$C_3$ alkyl and where $R_{4-4}$ and $R_{4-5}$ are taken together with the attached nitrogen atom to form a ring selected from the group consisting of 1-pyrrolidinyl, 1-piperidinyl, 1-morpholinyl, 4-pyrimidinyl optionally substituted in the 2 and/or 6-position with —$NR_{4-4}R_{4-5}$ where $R_{4-4}$ and $R_{4-5}$ are as defined above, piperid-3-en-1-yl optionally substituted in the 4-position with a member selected from the group consisting of —$\phi$ optionally substituted with I —$CF_3$, —Cl, —F, —$CH_3$, —$CH_2CH_3$, 2-pyridinyl optionally substituted in the 6-position with —$NR_{4-4}R_{4-5}$ where $R_{4-4}$ and $R_{4-5}$ are the same or different and are —H, $C_1$-$C_3$alkyl and where $R_{4-4}$ and $R_{4-5}$ are taken together with the attached nitrogen atom to form a ring selected from the group consisting of 1-pyrrolidinyl, 1-piperidinyl, 1-morpholinyl, 4-pyridinyl optionally substituted in the 2 and/or 6-position with —$NR_{4-4}R_{4-5}$ where $R_{4-4}$ and $R_{4-5}$ are as defined above, and pharmaceutically acceptable salts thereof.

Further disclosed is a method of treating resistance to cancer chemotherapeutic agents in human cancer patients which comprises administering to that human an effective amount of a sensitizing tricyclic compound of formula (V)

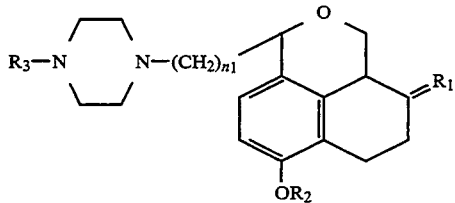

(V)

where:

$n_1$ is 1 thru 3, $R_1$ is $\alpha\text{-}R_{1\text{-}1}$:$\beta\text{-}R_{1\text{-}2}$ where $R_{1\text{-}1}$ and $R_{1\text{-}2}$ are the same or different and are —H, $C_1$-$C_3$ alkyl, $R_2$ is $C_1$-$C_3$ alkyl, $R_3$ is —$\phi$ optionally substituted with 1 thru 3 —F, —Cl, $C_1$—$C_3$ alkyl and pharmaceutically acceptable salts thereof.

Also disclosed are indoles of formula (VI)

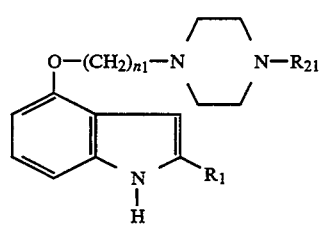

(VI)

and a method of treating resistance to cancer chemotherapeutic agents in human cancer patients which comprises administering to that human an effective amount of a sensitizing indole of formula (VI) where:

$R_1$ is —C—N or—CO—NH2;

$n_1$ is 1 thru 5;

$R_{21}$ is (1) $R_{21\text{-}28}$-CO—$(CH_2)_j$— where $R_{21\text{-}28}$ is -Aryl, —NR$_{21\text{-}29}$Aryl and 2-furanyl, where $R_{21\text{-}29}$ is —H or $C_1$-$C_3$ alkyl, where j is 0 thru 3 and Aryl is phenyl optionally substituted with 1 or 2 —Cl, —Br, $C_1$-$C_3$ alkoxy, —COOH, —NH$_2$, $C_1$-$C_3$ alkylamino, di($C_1$-$C_3$)alkylamino where the alkyl groups are the same or different, 1-pyrrolidinyl, 1-piperidinyl, 1-hexamethylenimino, 1-heptamethylenimino, $C_2$-$C_4$ acylamino and —NH—CHO or with 1 —F or —CF$_3$; (F-31)

(2) Heteroaryl-$(CH_2)_j$—, where Heteroaryl is (a) pyridin-2- (F-1), 3- (F-2) or 4-yl (F-3) or the N-oxide thereof optionally substituted by 1 or 2 $R_{21\text{-}2}$, being the same or different, where $R_{21\text{-}2}$ is (i) —F, (ii) —Cl, (iii) —Br, (iv) $C_1$-$C_5$ alkyl, (v) —CH$_2$-CH=CH$_2$, (vi) -Aryl, where Aryl is as defined above, (vii) —NR$_{21\text{-}3}$R$_{21\text{-}3}$ where the $R_{21\text{-}3}$'s are the same or different and are —H, Cl—$C_3$ alkyl or —CH$_2$-CH=CH$_2$, (viii$\alpha$) *CH$_2$—$(CH_2)_q$—CH$_2$—N*— where the atoms marked with an asterisk (*) are bonded to each other resulting in the formation of a ring, where q is 1 thru 5, (viii$\beta$) *CH$_2$-CH$_2$—$(CH_2)_c$—G—$(CH_2)_d$—CH$_2$-CH$_2$—N*— where the atoms marked with an asterisk (*) are bonded to each other resulting in the formation of a ring (F-4), where G is —O—, —S—, —SO—, —SO$_2$— or —NHR$_{21\text{-}4}$, where $R_{21\text{-}4}$ is —H, $C_1$-$C_3$ alkyl, or Aryl as defined above, where c and d are the same or different and are 0 thru 2 with the proviso that the total number of ring carbon atoms is 4, 5 or 6, (ix) 3-pyrrolin-1-yl, (F-5)

(x) pyrrol-1-yl optionally substituted with $C_1$-$C_3$ alkyl, (F-6)

(xi) piperidin-1-yl optionally substituted with 1 or 2 $C_1$-$C_3$ alkyl, (F-7)

(xii) 1,2,3,6-tetrahydropyridin-1-yl, (F-8)

(xiii) 1-hexanethyleneimino containing a 3- or 4- double bond or 3- and 5- double bonds, (F-9)

(xiv) 1,4-dihydro-1-pyridinyl substituted in the 4 position by two $C_1$-$C_3$ alkyl being the same or different, (F-10)

(xv) —OH, (xvi) $C_1$-$C_3$ alkoxy, (xvii) —NR$_{21\text{-}7}$(CH$_2$)$_e$—Q where Q is 2-pyridinyl where $R_{21\text{-}7}$ is —H or $C_1$-$C_3$ alkyl and e is 0 thru 3, (xviii) pyridin-2-, 3- or 4-yl, (b) 1,3,5-triazin-2-yl or the N-oxide thereof optionally substituted at the 4- and/or 6- position with $R_{21\text{-}2}$ is as defined above, (F-11)

(c) pyrimidin-4-yl or the N-oxide thereof optionally substituted at the 2- and/or 6- position with $R_{21\text{-}2}$ is as defined above, (F-12)

(d) pyrimidin-2-yl optionally substituted at 4- and/or 6- position with 1 or 2 $R_{21\text{-}2}$ as is defined above, (F-13)

(e) pyrazin-2-yl optionally substituted with 1 or 2 $R_{21\text{-}2}$ as is defined above, (F-14)

(f) imidazol-2-yl optionally substituted in the 1 position with $C_1$-$C_3$ alkyl or -Aryl, where Aryl is as defined above, and further optionally substituted with 1 or 2 $R_{21\text{-}2}$ as defined above, (F-15)

(g) 1,2,4-triazol-3-yl optionally substituted in the 1 position with $C_1$-$C_3$ alkyl or -Aryl, where Aryl is as defined above, and further optionally substituted with $R_{21\text{-}2}$ as defined above, (F-16)

(h) imidazol-4- or 5-yl optionally substituted in the 1 position with $C_1$-$C_3$ alkyl or -Aryl, where Aryl is as defined above, and further optionally substituted with 1 or 2 $R_{21\text{-}2}$ as defined above, (F-17)

(i) benzo[b]thien-2-yl, (F-18)

(j) indol-2-yl, (F-19)

(k) benzo[b]thiazol-2-yl, (F-20)

(l) benzimidazol-2-yl, (F-21)

(m) 4-[2-[4-[2,6-bis(1-pyrrolidinyl)-4-pyrimidinyl]-1-piperazinyl]ethyl]piperazinyl, (F-22)

(n) 1,2,4-triazol-3-yl optionally substituted at the 5- and/or 6- position with $R_{21\text{-}2}$ as is defined above, (F-23)

and where j is as defined above, (F-32)

(3) Aryl-$(CH_2)_j$—, where Aryl and j are as defined above, (F-33)

and pharmaceutically acceptable salts thereof.

DETAILED DESCRIPTION OF THE INVENTION

The steroidal amines (I) are known, see International Publication No. WO87/01706, published Mar. 26, 1987 based on International Patent Application No. PCT/US86/01797.

The alkyl amines (II) and the bicyclic amines (III) are known, see International Publication No. WO88/08424, published November 3, 1988 based on International Patent Application No. PCT/US88/012 12.

The bicyclic ethers (IV) are known, see for example, U.S. Pat. Nos. 4,206,123, 4,577,021, 4,711,960 and 4,487,774.

The tricyclic amines (V) are known see U.S. Pat. No. 4,487,774.

The indole amines (VI) are prepared by the process set forth in EXAMPLES 5–8.

With either the steroidal amines (I), alkyl amines (II) or bicyclic amines (III), it is preferred that the amine portion be cyclized, that is $R_{21-\alpha}$ and $R_{21-\beta}$ be taken together with the attached nitrogen atom to form a heterocyclic ring which is group (C). It is further preferred that the heterocyclic ring be piperazinyl substituted with either Aryl or Heteroaryl, preferably with Heteroaryl. It is preferred that the Heteroaryl substituent itself be substituted, more preferably be di substituted. It is preferred that the substituents on the Heteroaryl group themselves be cyclized such as pyrolidinyl.

It is preferred that the steroidal amine (I) be

17α-hydroxy-21-[4-(2-pyridinyl)-1-piperazinyl]-pregna-4,9(11)-diene-3,20-dione,

21-[4-(2,6-di-1-pyrrolidinyl)-4-pyrimidinyl-1-piperazinyl]-16α-methylpregna-1,4,9(11)-triene-3,20-dione, 21 -[4-(2,6-di-1-pyrrolidinyl)-4-pyrimidinyl-1-piperazinyl]pregna-1,4,9(11)-triene-3,20-dione, 21 -[4-3,6-bis(diethylamino)-2-pyridinyl]-1-piperazinyl-16α-methylpregna-1,4,9( 11)-triene-3,20-dione, 21 -[4-(4,6-di-1-pyrrolidinyl-1,3,5-triazin-2-yl)-1-piperazinyl]-16α-methylpregna-1,4,9(11)-triene-3,20-dione, 21 -[4-[3-(ethylamino)-2-pyridinyl]-1-piperazinyl-16α-methylpregna-1,4,9(11)-triene-3,20-dione, 21-[4-(4,6-di-1-pyrrolidinyl-2-pyrimidinyl)-1-piperazinyl]-16α-methylpregna-1,4,9(11)-triene-3,20-dione. It is more preferred that the steroidal amine (I) be 17α-hydroxy-21-[4-(2-pyridinyl)-1-piperazinyl]-pregna-4,9(11)-diene-3,20-dione, 21-[4-2,6-di-1-pyrrolidinyl)-4-pyrimidinyl-1-piperazinyl]-16α-methylpregna-1,4,9(11)-triene-3,20-dione, 21 -[4-(2,6-di-1-pyrrolidinyl)-4-pyrimidinyl-1-piperazinyl]pregna-1,4,9(11)-triene-3,20-dione, 21-[4-[3-(ethylamino)-2-pyridinyl]-1-piperazinyl-16α-methylpregna-1,4,9(11)-triene-3,20-dione. It is even more preferred that the steroidal amine be 21-[4-2,6-di-1-pyrrolidinyl)-4-pyrimidinyl-1-piperazinyl]-16α-methylpregna-1,4,9(11)-triene-3,20-dione.

It is preferred that the alkyl amines (II) be 4-(2,6-di-1-pyrrolidinyl-4-pyrimidinyl)-1-piperazinehexanol, 4-(2,6-di-1-pyrrolidinyl-4-pyrimidinyl)-1-piperazineoctanol, 4-[[6-[4-(2,6-di-1-pyrrolidinyl-4-pyrimidinyl)-1-piperazinyl]hexyl]oxy]phenol, 4-(2,6-di-1-pyrrolidinyl-4-pyrimidinyl)-α-phenyl-1-piperazinebutanol, 4-[3-[4-(2,6-di-1-pyrrolidinyl-4-pyrimidinyl)-1-piperazinyl]propyl]-2,6-dimethylphenol, 4-(2,6-di-1-pyrrolidinyl-4-pyrimidinyl)-1-piperazineheptanoic acid methyl ester. It is more preferred that the alkyl amines (II) be 4-(2,6-di-1-pyrrolidinyl-4-pyrimidinyl)-1-piperineoctanol, 4-(2,6-di-1-pyrrolidinyl-4-pyrimidinyl)-α-phenyl-1-piperazinebutanol.

It is preferred that the bicyclic amines (III) be

2-[[4-(2,6-di-1-pyrrolidinyl-4-pyrimidinyl)-1-piperazinyl]methyl]-3,4-dihydro-2,5,7,8-tetramethyl-2H-1-benzopyran-6-ol, 2-[[4-3-(ethylamino)-2-pyridinyl]-1-puperazinyl]methyl]-3,4-dihydro-2,5,7,8-tetramethyl2H-1-benzopyran-6-ol, 3-[4-(2,6-di-1-pyrrolinyl-4-pyrimidinyl)-1-piperazinyl]-6-(acetyloxy)-3,4-dihydro-2,5,7,8-tetramethyl-2H-1-benzopyran-2-carboxylic acid propyl ester, 1-[3-(ethylamino)-2-pyridinyl]-4-[(5-methoxy-4,6,7-trimethyl-1H-indol-2-yl)carbonyl]piperazine. It is more preferred that the bicyclic amine (III) be 2-[[4-(2,6-di-1-pyrrolidinyl-4-pyrimidinyl)-1-piperazinyl]-methyl-3,4-tetramethyl-2H-1-benzopyran-6-ol, 2-[[4-3-(ethylamino)-2-pyridinyl]-1-piperazinyl]methyl]-3,4-dihydro-2,5,7,8-tetramethyl2H-1-benzopyran-6-ol.

It is preferred that the bicyclic ethers (IV) be

1 -[(3,4-dihydro-6,7-dimethoxy- 1H-2-benzopyran-1-yl)methyl]-4-[3-(trifluoromethyl)phenyl]piperazine, 1-[(3,4-dihydro-6,7-dimethoxy-1H-2-benzopyran-1-yl)methyl]-4-(2-methylphenyl)piperazine, 1-[(3,4-dihydro-8-methoxy-1H-2-benzopyran-1-yl)methyl]-4-(2-methylphenyl)piperazine, 4-(4-chlorophenyl)-1-[2-(3,4-dihydro-6,7-dimethoxy-1H-2-benzopyran-1-yl)ethyl]-1,2,3,6-tetrahydropiperidine, 1-[2-(3,4-dihydro-6,7-dimethoxy-1H-2-benzopyran-1-yl)ethyl]-4-(2-methylphenyl)piperazine, 1 -(2-chlorophenyl)-4-[2-(3,4-dihydro-6,7-dimethoxy-1H-2-benzopyran-1-yl)ethyl]piperazine, 1 -[2-(3,4-dihydro-6,7-dimethoxy-4,4-dimethyl- 1H-2-benzopyran-1-yl)ethyl]-4-(4-fluorophenyl)piperazine, 1-[2-(3,4-dihydro-6,7-dimethoxy-4,4-dimethyl-1H-2-benzopyran-1-yl)ethyl]-4-[3-(trifluoromethyl)phenyl]-piperazine, 1 -(4-chlorophenyl)-4-[2-(3,4-dihydro-6,7-dimethoxy-4,4-dimethyl-1H-2-benzopyran-1 -yl)ethyl]piperazine, 1-[2-(3,4-dihydro-6,7-dimethoxy-4,4-dimethyl -1H-2-benzopyran-1-yl)ethyl]-4-(2-methylphenyl)piperazine, 1 -[2-(3,4-dihydro-6,7-dimethoxy-4,4-dimethyl-1H-2-benzopyran-1-yl)ethyl]-1,2,3,6-tetrahydro-4-phenylpyridine, 2-[2-(3,4-dihydro-6,7-dimethoxy-4,4-dimethyl-1H-2-benzopyran-1-yl)ethyl]-1,2,3,5-tetrahydro-6,7-dimethoxyisoquinoline, 1-[2-(3,4-dihydro-5,6-dimethoxy-4,4-dimethyl-1H-2-benzopyran-1-yl)ethyl]-4phenylpiperazine, 1 -(4-fluorophenyl)-4-(3-[1-(4-fluorophenyl)-3,4-dihydro-6,7-dimethoxy-1H-2-benzopyran-1-yl]-propyl]piperazine, 1-[3-[1-(4-fluorophenyl)-3,4-dihydro-6,7-dimethoxy-1H-2-benzopyran-1-yl]propyl]-4-(2-methylphenyl)piperazine, 1 -[3-[1 -(4-fluorophenyl)-3,4-dihydro-6,7-dimethoxy-1H-2-benzopyran-1-yl]propyl]-4-phenylpiperazine, 2H—Benzimidazol-2-one, 1-[1-[3-[14-fluorophenyl)-3,4-dihydro-6,7-dimethoxy-1H-2-benzopyran-1-yl]-propyl]-4-piperidinyl]-1,3-dihydropiperazine, 1-[3-[1(4-fluorophenyl)-3,4-dihydro-6,7-dimethoxy-1H-2-benzopyran-1-yl]propyl]-4-(2-pyridinyl)piperazine, 1-[2-(3,4-dihydro-6,7-dimethoxy-4-methyl- 1H-2-benzopyran-1-yl)ethyl]-1,2,3,6-tetrahydro-4-phenylpyridine, 1-[2-(3,4-dihydro-6,7-dimethoxy-4-methyl- 1H-2-benzopyran-1-yl)ethyl]-4-(2methylphenyl)piperazine, 1-(2-chlorophenyl)-4- [2-(3,4-dihydro-6,7-dimethoxy-4-methyl-1H-2-benzopyran-1-yl)ethyl]piperazine, 1-[3-(3,4-dihydro-6,7-dimethoxy-1,4,4-trimethyl-1H-2-benzopyran-1-yl)propyl]-4-phenylpiperazine, 1-[3-(3,4-dihydro-6,7-dimethoxy-1,4,4-trimethyl-1H-2-benzopyran-1-yl)propyl]-4-(2-methylphenyl)piperazine, 1-[3-(3,4-dihydro-6,7-dimethoxy-1,4,4-trimethyl-1H-2-benzopyran-1-yl)propyl]-4-(4-fluorophenyl)piperazine, 1-[3-[1-(4-fluorophenyl)-3,4-dihydro-6,7-dimethoxy-4,4-dimethyl-1H-2-benzopyran-1-yl]propyl]-4-phenylpiperazine, 1-[3-[1-(4-fluorophenyl)-3,4-dihydro-6,7-dimethoxy-4-methyl-1H-2-benzopyran-1-yl]propyl]-1,2,3,6-tetrahydro-4-phenylpyridine, 1-[3-(3,4-dihydro-6,7-dimethoxy-1,4-dimethyl-1H-2-benzopyran-1-yl)propyl]-1,2,3,6-tetrahydro-4-phenylpyridine, 1-[3-[1-(4-fluorophenyl)-3,4-dihydro-6,7-dimethoxy-4-methyl-1H-2-benzopyran-1-yl]propyl-4-phenylpiperazine, 1-(3-chloropropyl)-1-(4-fluorophenyl)-3,4-dihydro-6,7-dimethoxy-4,4-dimethyl-1H-2benzopyran, 1-[3-(3,4-dihydro-6,7-dimethoxy-1,4,4-trimethyl-1H-2-benzopyran-1-yl)propyl]-1,2,3,6-tetrahydro-4-phenylpyridine, 1-[3-(3,4-dihydro-6,7-dimethoxy-1,4-dimethyl-1H-2-benzopyran-1-yl)propyl]-4-(2-methylphenyl)piperazine, 1-(2-chlorophenyl)-4-[2-(3,4-dihydro-6,7-dimethoxy-1-methyl-1H-2-benzopyran-1-yl)ethyl]piperazine, 1-(3 -chlorophenyl)-4-[2-(3,4-dihydro-6,7-dimethoxy-4,4-dimethyl-1H-2-benzopyran-1-yl)ethyl]piperazine, 1-(3-chlorophenyl)-4-[2-(3,4-dihydro-6,7-dimethoxy-4-methyl-1H-2-benzopyran-1-yl)ethyl]piperazine, 6-[4-[2-(3,4-dihydro-6,7-dimethoxy- 1H-2-benzopyran-1-yl)ethyl]-1-piperazinyl]-N,N,N',N'-tetraethyl-2,4-pyrimidinediomine, 4-[4-[2-(3,4-dihydro-6,7-dimethoxy- 1H-2-benzopyran-1-yl)ethyl]-1-piperazinyl]-2,6-di-1-pyrrolidinyl-pyrimidine. It is more preferred that the bicyclic ethers (IV) be 1- [(3,4-dihydro-6,7-dimethoxy-1H-2-benzopyran-1-yl)methyl]-4-(2-methylphenyl)piperazine, 1-[2-(3,4-dihydro-6,7-dimethoxy-4,4-dimethyl-1H-2-benzopyran-1-yl)ethyl]-4-(2-methylphenyl)piperazine, 1-[2-(3,4-dihydro-6,7-dimethoxy-4-methyl-1H-2-benzopyran-1-yl)ethyl]-4-(2-methylphenyl)piperazine, 1- [3-[1-(4-fluorophenyl)-3,4-dihydro-6,7-dimethoxy-4-methyl-1H-2-benzopyran-1-yl]propyl]-1,2,3,6-tetrahydro-4-phenylpyridine, 1-(3 -chlorophenyl)-4-[2-(3,4-dihydro-6,7-dimethoxy-4,4-dimethyl-1H-2-benzopyran-1-yl)ethyl]piperazine, 4-[4-[2-(3,4-dihydro-6,7-dimethoxy- 1H-2-benzopyran-1-yl)ethyl]-1-piperazinyl]-2,6-di-1-pyrrolidinyl-pyrimidine.

It is most preferred that the bicyclic ethers (IV) be 1-[2-(3,4-dihydro-6,7-dimethoxy-4,4-dimethyl-1H-2-benzopyran-1-yl)ethyl]-4-(2-methylphenyl)piperazine.

It is preferred that the tricyclic amines (V) be
1-(4-fluorophenyl)-4-[2-(3a,4,5,6-tetrahydro-7-methoxy-4,4-dimethyl-1H-3H-naphthol[1,8-cd]pyran-1-yl)-ethyl]piperazine, 1-(2-methylphenyl)-4-[2-(3 a,4,5,6-tetrahydro-7-methoxy-4,4-dimethyl-1H-3H-naphtho]1,8-cd]pyran-1-yl)-ethyl]piperazine, 1-(2-chlorophenyl)-4-[2-(3a,4,5,6-tetrahydro-7 methoxy-4,4-dimethyl-1-H-3H-naphthol[1,8-cd]pyran-1-yl)-ethyl]piperazine. It is more preferred that the tricyclic amines (V) be 1-(2chlorophenyl)-4[2(3a4,5,6-tetrahydro-7-methoxy-4,4-dimethyl-1H-3H-naphthol[1,8-cd]pyran-1-yl)-ethyl]piperazine.

It is preferred that the indole amines (VI) be
4-[3-4-diphenylmethyl)-1-piperazinyl]propoxy]indole-2-carboxamide, 4-[3-[4-[2,4-dipyrrolidino-6-pyrimidinyl]-1-piperazinyl]propoxy]indol-2-carboxamide, 2-cyano-4-[3-[4-(diphenylmethyl)-1-piperazinyl]-propoxy]indole, 2-cyano-4-[3-[4-(2,4-dipyrrolidino-6-pyrimidinyl)-1-piperazinyl]propoxy]indole. It is more preferred that the indolemines (VI) be 4-[3-4-diphenylmethyl)-1-piperazinyl]propoxy]-indole-2-carboxamide.

Other compounds which are useful in the present invention are
11-[[4-(2,6-di-1-pyrrolidinyl-4-pyrimidinyl)-1-piperazinyl]acetyl]oxy]-16α-methylpregn-4-en-3,20-dione, 4-[5-(benzoyloxy)-2,6-di-1-pyrrolidinyl-4-pyrimidinyl]1-piperazineheptanoic acid methyl ester, 21-[4-(2,6-di-1-pyrrolidinyl-5-(4-chlorobenzoyloxy))4-pyrimidinyl-1-piperazinyl]-16α-methylpregna-1,4,9(11)-triene-3,20-dione, 3-[2-[4-[3-(ethyl amino)-2-pyridinyl]-1-piperazinyl]ethyl]octahydro-7-[2-(5-hydroxy-2-methylphenyl)ethyl]-3a-methyl-5H-inden-5-one.

It is preferred mat the sensitizing compound be selected from the group consisting of
1-[(3,4-dihydro-6,7-dimethoxy-1H-2-benzopyran-1-yl)methyl]-4-(2-methylphenyl)piperazine, 1-[2-(3,4-dihydro-6,7-dimethoxy4,4-dimethyl-1H-2-benzopyran-1-yl)ethyl]4-(2-methylphenyl)piperazine, 1-[2-(3,4-dihydro-6,7-dimethoxy4-methyl-1H-2-benzopyran-1-yl)ethyl]-4-(2-methylphenyl)piperazine, 1-[3-[1-(4-fluorophenyl)-3,4-dihydro-6,7-dimethoxy4-methyl-1H-2-benzopyran-1-yl]propyl]-1,2,3,6-tetrahydro-4-phenylpyridine, 1-(3 -chlorophenyl)4-[2-(3,4-dihydro-6,7-dimethoxy4,4-dimethyl-1H-2-benzopyran-1-yl)ethyl]piperazine, 11-[[4-(2,6-di-1-pyrrolidinyl 4-pyrimidinyl)-1-piperazinyl]acetyl]oxy]-16α-methylpregn-4-en-3,20-dione, 21-[4-(2,6-di-1-pyrrolidinyl)-4-pyrimidinyl-1-piperazinyl]-16α-methylpregna-1,4,9(11)-triene-3,20-dione, 4-[4-[2 -( 3,4-dihydro -6,7 - dimethoxy -1H -2 -benzopyran-1-yl)ethyl]-1-piperazinyl]-2,6-di-1-pyrrolidinyl-pyrimidine, 21-[4-[3 -(ethyl amino)-2 -pyridinyl]-1-piperazinyl-16a-methylpregna-1,4,9(11)-triene-3,20-dione, 4-(2,6-di-1-pyrrolidinyl-4-pyrimidinyl)-α-phenyl-1-piperazinebutanol, 4-[34-diphenylmethyl)-1-piperazinyl]propoxy]indole-2-carboxamide, 4-[5-(benzoyloxy)-2,6-di-1-pyrrolidinyl-4-pyrimidinyl]1-piperazineheptanoic acid methyl ester.

The sensitizing compounds of this invention are mines and as such form acid addition salts when reacted with acids of sufficient strength. Pharmaceutically acceptable salts include salts of both inorganic and organic acids. The pharmaceutically acceptable salts are preferred over the corresponding free amines since they produce compounds which are more water soluble and more crystalline. The preferred pharmaceutically acceptable salts include salts of the following acids methanesulfonic, hydrochloric, hydrobromic, sulfuric, phosphoric, nitric, benzoic, citric, tartaric, fumaric, maleic, $CH_3—(CH_2)_n—COOH$ where n is 0 thru 4, $HOOC—(CH_2)_n—COOH$ where n is as defined above.

Further, the sensitizing compounds and salts thereof form solvates and hydrates thereof, as is known in the art, which are equivalent to the nonsolvated or nonhydrated forms.

The term "treating" as used in this invention means both (1) preventing resistance to the chemotherapeutic agents and (2) overcoming resistance to the chemotherapeutic agents which already exists.

Further, "preventing" means to prevent all-together or to slow the pace at which resistance develops.

The method of the present invention is useful in sensitizing desensitized cancer cells of the following types of cancer: ovarian, sarcoma, non-Hodgkin's lymphoma, lung, breast cancer, bladder carcinoma, colon carcinoma, pancreatic carcinoma, carcinoma of the ampulla of Vater, multiple myeloma, adult acute lymphocytic leukemia, adult non-lymphoytic leukemia and neuroblastoma. It is preferred that the cancer cells be breast cancer, multiple myeloma, ovarian or lung.

It is realized that the desensitized cancer cells may be desensitized to more than one chemotherapeutic agent. If so, the method of the present invention will sensitize the desensitized cancer cells to most of the chemotherapeutic agents to which they are desensitized.

The chemotherapeutic agents to which the cancer cells become desensitized are selected from the group consisting of doxorubicin, daunomycin, vinca alkaloids, vincristine, vinblastine, taxol, colchicine, epipodophyllotoxins such as etoposide, actinomycin D, puromycin, emetine, melphalan, adozelesin,

[S-(R,R)]6,6'-[carbonylbis(imino-1H-indole-5,2-diyl-carbonyl)]bis[8-(chloromethyl)-3,6,7,8 -tetrahydro-1-,methyl -benzo [1,2-b;4, 3 -b']dipyrrol-4-ol, (S)—N-[2-[[1-(chloromethyl)-1,6-dihydro-8 -methyl-5 -[[(phenylamino)carbonyl]opxy]benzo[1,2-b:4,3-b']dipyrrol-3(2H)-yl]carbonyl]-1H-indol-5-yl]-6-(diethylamino)-2-benzofurancarboxamide, (7bR,8 aS)-7-[[1,6-dihydro-4-hydroxy-5 -methoxy-7-[(4,5,8,8a-tetrahydro-7-methyl-4-oxocyclopropa[c]pyrrolo[3,2-e]indol-2( 1H)-yl)carbonyl]benzo[1,2-b:4,3-b']dipyrrol-3(2H)yl]carbonyl]-1,6-dihydro-4-hydroxy-5-methoxybenzo[1,2-b:4,3-b']dipyrrole-3(2H)-carboxamide. It is preferred that the chemotherapeutic agent be selected from the group consisting of doxorubicin or vincristine.

It is realized that new chemotherapeutic agents against cancer will be developed after this invention. The new chemotherapeutic agents to which resistance develops and which can be treated by the method of this invention are equivalent to those set forth in this invention.

The sensitizing compounds of the present invention are used as discussed below. Patients with cancer which once responded to a chemotherapeutic agent(s) and which now responds to the chemotherapeutic agent in a much poorer way, are pre-treated with the sensitizing compound for about 12-36 hours, preferably about 24 hrs, before treatment with the desired chemotherapeutic agent(s) is resumed. Once treatment is reinstated with the chemotherapeutic agent, the sensitizing compound and chemotherapeutic agent(s) is administered concurrently. Alteratively, in individuals who have cancer and who have not been previously treated with chemotherapeutic agents, the sensitizing compounds of this invention are given when the chemotherapeutic agents are initially given to either totally prevent resistance from developing or slow the rate at which the resistance develops.

An effective amount of the sensitizing compound is from about 1 mg/kg/day to about 500 mg/kg/day, preferably from about 1 mg/kg/day to about 100 mg/kg/day, more preferably from about 5 mg/kg/day to about 75 mg/kg/day.

The sensitizing compound is administered IV, orally and IP. When administered IV it is given continuously. When it is administered orally it is given 3 or 4 times daily in divided doses.

The various sensitizing compounds of this invention need not be used separately. They can be used in combination with each other or with other known sensitizing compounds.

The exact dosage and frequency of administration depends on the particular sensitizing compound(s) used, the particular condition being treated, the severity of the condition being treated, the age, weight, general physical condition of the particular patient, other medication the individual may be taking as is well known to those skilled in the an and can be more accurately determined by measuring the blood level or concentration of the sensitizing compound(s) in the patient's blood and/or the patient's response to the particular condition being treated.

Whether or not a compound is a good sensitizing compound can readily be determined by known means, see *Cancer Letters* 50, 45–51 (1990).

DEFINITIONS AND CONVENTIONS

The definitions and explanations below are for the terms as used throughout this entire document including both the specification and the claims.

I. CONVENTIONS FOR FORMULAS AND DEFINITIONS OF VARIABLES

The chemical formulas representing various compounds or molecular fragments in the specification and claims may contain variable substituents in addition to expressly defined structural features. These variable substituents are identified by a letter or a letter followed by a numerical subscript, for example, "$Z_1$" or "$R_i$" where 'T' is an integer. These variable substituents are either monovalent or bivalent, that is, they represent a group attached to the formula by one or two chemical bonds. For example, a group $Z_1$ would represent a bivalent variable if attached to the formula $CH_3—C(=Z_1)H$. Groups $R_i$ and $R_j$ would represent monovalent variable substituents if attached to the formula $CH_3—CH_2—C(R_i)(R_j)—H$. When chemical formulas are drawn in a linear fashion, such as those above, variable substituents contained in parentheses are bonded to the atom immediately to the left of the variable substituent enclosed in parenthesis. When two or more consecutive variable substituents are enclosed in parentheses, each of the consecutive variable substituents is bonded to the immediately preceding atom to the left which is not enclosed in parentheses. Thus, in the formula above, both $R_i$ and $R_j$ are bonded to the preceding carbon atom. Also, for any molecule with an established system of carbon atom numbering, such as steroids, these carbon atoms are designated as $C_i$, where "i" is the integer corresponding to the carbon atom number. For example, $C_6$ represents the 6 position or carbon atom number in the steroid nucleus as traditionally designated by those skilled in the art of steroid chemistry. Likewise the term "$R_6$" represents a variable substituent (either monovalent or bivalent) at the $C_6$ position.

Chemical formulas or portions thereof drawn in a linear fashion represent atoms in a linear chain. The symbol "—" in general represents a bond between two atoms in the chain. Thus $CH_3$—O—$CH_2$—CH-($R_i$)—$CH_3$ represents a 2-substituted-1-methoxypropane compound. In a similar fashion, the symbol "=" represents a double bond, e.g., $CH_2$=C($R_i$)—O—$CH_3$, and the symbol "≡" represents a triple bond, e.g., HC≡C—CH($R_i$)—$CH_2$—$CH_3$. Carbonyl groups are represented in either one of two ways: —CO— or —C(=O)—, with the former being preferred for simplicity.

Chemical formulas of cyclic (ring) compounds or molecular fragments can be represented in a linear fashion. Thus, the compound 4-chloro-2-methylpyridine can be represented in linear fashion by N*=C($CH_3$)—CH=CCl—CH=C*H with the convention that the atoms marked with an asterisk (*) are bonded to each other resulting in the formation of a ring. Likewise, the cyclic molecular fragment, 4-(ethyl)-1-piperazinyl can be represented by —N*—($CH_2$)$_2$—N($C_2H_5$)—$CH_2$—C*$H_2$.

A rigid cyclic (ring) structure for any compounds herein defines an orientation with respect to the plane of the ring for substituents attached to each carbon atom of the rigid cyclic compound. For saturated compounds which have two substituents attached to a carbon atom which is part of a cyclic system, —C($X_1$)($X_2$)— the two substituents may be in either an axial or equatorial position relative to the ring and may change between axial-/equatorial. However, the position of the two substituents relative to the ring and each other remains fixed. While either substituent at times may lie in the plane of the ring (equatorial) rather than above or below the plane (axial), one substituent is always above the other. In chemical structural formulas depicting such compounds, a substituent ($X_1$) which is "below" another substituent ($X_2$) will be identified as being in the alpha ($\alpha$) configuration and is identified by a broken, dashed or dotted line attachment to the carbon atom, i.e., by the symbol "- - -" or "...". The corresponding substituent attached "above" ($X_2$) the other ($X_1$) is identified as being in the beta ($\beta$) configuration and is indicated by an unbroken line attachment to the carbon atom.

When a variable substituent is bivalent, the valences may be taken together or separately or both in the definition of the variable. For example, a variable $R_i$ attached to a carbon atom as —C(=$R_i$)— might be bivalent and be defined as oxo or keto (thus forming a carbonyl group (—CO—) or as two separately attached monovalent variable substituents $\alpha$-$R_{i-j}$ and $\beta$-$R_{i-k}$. When a bivalent variable, $R_i$, is defined to consist of two monovalent variable substituents, the convention used to define the bivalent variable is of the form "$\alpha$-$R_{i-j}$:$\beta$-$R_{i-k}$" or some variant thereof. In such a case both $\alpha$-$R_{i-j}$ and $\beta$-$R_{i-k}$ are attached to the carbon atom to give —C($\alpha$-$R_{i-j}$) (15-$R_{i-k}$)—. For example, when the bivalent variable $R_6$, —C(=$R_6$)— is defined to consist of two monovalent variable substituents, the two monovalent variable substituents are $\alpha$-$R_{6-1}$:$\beta$-$R_{6-2}$ ... $\alpha$-$R_{6-9}$:$\beta$-$R_{6-10}$, etc, giving —C($\alpha$-$R_{6-1}$)($\beta$-$R_{6-2}$)—... —C($\alpha$-$R_{6-9}$)($\beta$-$R_{6-10}$)—, etc. Likewise, for the bivalent variable $R_{11}$, —C(=$R_{11}$)—, two monovalent variable substituents are $\alpha$-$R_{11-1}$:$\beta$-$R_{11-2}$. For a ring substituent for which separate $\alpha$ and $\beta$ orientations do not exist (e.g. due to the presence of a carbon carbon double bond in the ring), and for a substituent bonded to a carbon atom which is not part of a ring the above convention is still used, but the $\alpha$ and $\beta$ designations are omitted.

Just as a bivalent variable may be defined as two separate monovalent variable substituents, two separate monovalent variable substituents may be defined to be taken together to form a bivalent variable. For example, in the formula —$C_1$($R_i$)H—$C_2$($R_j$)H—($C_1$ and $C_2$ define arbitrarily a first and second carbon atom, respectively) $R_i$ and $R_j$ may be defined to be taken together to form (1) a second bond between $C_1$ and $C_2$ or (2) a bivalent group such as oxa (—O—) and the formula thereby describes an epoxide. When $R_i$ and $R_j$ are taken together to form a more complex entity, such as the group —X—Y—, then the orientation of the entity is such that $C_1$ in the above formula is bonded to X and $C_2$ is bonded to Y. Thus, by convention the designation "... $R_i$ and $R_j$ are taken together to form —$CH_2$—$CH_2$—O—CO—..." means a lactone in which the carbonyl is bonded to $C_2$. However, when designated "... $R_j$ and $R_i$ are taken together to form —CO—O—$CH_2$—$CH_2$— the convention means a lactone in which the carbonyl is bonded to $C_1$.

The carbon atom content of variable substituents is indicated in one of two ways. The first method uses a prefix to the entire name of the variable such as "$C_1$-$C_4$", where both "1" and "4" are integers representing the minimum and maximum number of carbon atoms in the variable. The prefix is separated from the variable by a space. For example, "$C_1$-$C_4$ alkyl" represents alkyl of 1 through 4 carbon atoms, (including isomeric forms thereof unless an express indication to the contrary is given). Whenever this single prefix is given, the prefix indicates the entire carbon atom content of the variable being defined. Thus $C_2$-$C_4$ alkoxycarbonyl describes a group $CH_3$—($CH_2$)$_n$—O—CO— where n is zero, one or two. By the second method the carbon atom content of only each portion of the definition is indicated separately by enclosing the "$C_i$-$C_j$" designation in parentheses and placing it immediately (no intervening space) before the portion of the definition being defined. By this optional convention ($C_1$-$C_3$)alkoxycarbonyl has the same meaning as $C_2$-$C_4$ alkoxycarbonyl because the "$C_1C_3$" refers only to the carbon atom content of the alkoxy group. Similarly while both $C_2$-$C_6$ alkoxyalkyl and ($C_1$-$C_3$)alkoxy($C_1$-$C_3$)alkyl define alkoxyalkyl groups containing from 2 to 6 carbon atoms, the two definitions differ since the former definition allows either the alkoxy or alkyl portion alone to contain 4 or 5 carbon atoms while the latter definition limits either of these groups to 3 carbon atoms.

When the claims contain a fairly complex (cyclic) substituent, at the end of the phrase naming/designating that particular substituent will be a notation in (parentheses) which will correspond to the same name/designation in one of the CHARTS which will also set forth the chemical structural formula of that particular substituent.

II. DEFINITIONS

Pharmaceutically acceptable refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability.

Treating means both (1) preventing resistance to the chemotherapeutic agents and (2) overcoming resistance to the chemotherapeutic agents which already exists.

Preventing means to prevent all-together or to slow the pace at which resistance develops.

Saline refers to a saturated aqueous sodium chloride solution.

TLC refers to thin-layer chromatograpy.

Ether refers to diethy ether.

EXAMPLES

Without further elaboration, it is believed that one skilled in the art can, using the preceding description, practice the present invention to its fullest extent. The following detailed examples describe how to perform the various processes of the invention and are to be construed as merely illustrative, and not limitations of the preceding disclosure in any way whatsoever. Those skilled in the art will promptly recognize appropriate variations from the procedures.

EXAMPLE 1

Non-Hodgkin's Lymphoma Treated With Doxorubin, Vincrinstine, Cyclophosphamide and Dexamethasone A 70 kg male patient with non-Hodgkin's Lymphoma was treated with doxorubin, vincrinstine, cyclophosphamide and dexamethasone and after a period of time the lymphoma did not respond as well as it did previously to the treatment. Therefore, to sensitize the lymphoma to further treatment with with these agents the patient is treated as follows:

21-[4-2,6-di-1-pyrrolidinyl)-4-pyrimidinyl-1-piperazinyl]-16α-methylpregna-1,4,9(11)-triene-3,20-dione [IV, 0.01 mg/kg/hr to 5.0 mg/kg/hr for days 1–5], cyclophosphamide [IV, 600 mg/m$^2$ on day 2], vincrinstine [IV, 24 hr infusion, 0.4 mg/day, days 2–5], doxorubicin [IV, 24 hr infusion, 10 mg/m$^2$/day, days 2–5], dexamethasone [orally, 40 mg/day, days 2–5].

The treatment is repeated every 3 to 4 weeks in the absence of severe systemic toxicities, see J. Clin Oncol. 9, 17 (1991).

EXAMPLE 2

Pancreatic Carcinoma Treated With Adriamycin

A 55 kg female patient with pancreatic carcinoma was treated with adriamycin and after a period of time the carcinoma did not respond as well as it did previously to the treatment. Therefore, to sensitize the carcinoma to treatment with adriamycin the patient is treated as follows:

4-[3-4-diphenylmethyl)-1-piperazinyl]propoxy]indole-2-carboxamide, [IV, 0.01 mg/kg/hr to 5.0 mg/kg/hr for days 1–5], adriamycin [IV, 50 mg/m$^2$/day for days 2–5].

The course of treatment is repeated every 3 weeks with adjustment of adriamycin dose if toxicities in blood counts or severe stomatitis are noted as is known to those skilled in the art; see Am. J. Clin. Oncol., 9, 355 (1986).

EXAMPLE 3

Breast Cancer Treated With Adriamycin

A 62 kg female patient with breast cancer was treated with adriamycin and after a period of time the cancer did not respond as well as it did previously to the treatment. Therefore, to sensitize the breast cancer to treatment with adriamycin the patient is treated as follows:

11-[[4-(2,6-di-1-pyrrolidinyl-4-pyrimidinyl)-1-piperazinyl]acetyl]oxy]-16α-methylpregn-4-en-3,20-dione, [IV, 50 mg/kg/day, over 15–20 min four times a day on days 1–6], adriamycin [IV infusion at 60 mg/day on days 2–6]

The course of treatment is repeated every 3 to 4 weeks in the absence of severe systemic toxicity; see J. Clin. Oncol., 6, 880 (1988).

EXAMPLE 4

Multiple Myeloma Treated with Vincrinstine, Doxorubicin, Dexamethasone, and Cyclophosphamide A 75 kg male with diagnosed multiple myeloma (who has never been treated for cancer previously) is treated as follows:

1-[2-(3,4-dihydro-6,7-dimethoxy-4,4-dimethyl-1H-2-benzopyran-1-yl)ethyl]-4-(2-methylphenyl)piperazine, [IV, 0.01 mg/kg/hr to 5.0 mg/kg/hr for days 1–5], cyclophosphamide [IV, 600 mg/m$^2$ on day 2], vincrinstine [IV, 24 hr infusion, 0.4 mg/day, days 2–5], doxorubicin [IV, 24 hr infusion, 10 mg/m$^2$/day, days 2–5], dexamethasone [orally, 40 mg/day, days 2–5].

The treatment is repeated every 3 to 4 weeks in the absence of severe systemic toxicities, see J. Clin Oncol. 9, 17 (1991).

EXAMPLE 5

4-[3-[4-(Diphenylmethyl)-1-piperazinyl]propoxy]indole-2-carboxamide (VI)

4-(Benzyloxy)indole-2-carboxylic acid Imp 239°–241° d., lit. mp 241°–242° d.](15.0 g) in 250 ml of methylene chloride and 3 ml of DMF is treated dropwise, under nitrogen, with 4.2 ml (6.85 g) of thionyl chloride in 65 ml of methylene chloride over 10 min. The mixture is stirred at 20°–25° for 2.5 hr, 250 ml of ether is added, a −20° bath was applied, and ammonia (gas) is bubbled through the mixture for 30 min. The mixture is stirred as the bath temperature was allowed to rise from −20° to 10° over 1 hr. After another hour at 20°–25° the mixture is bubbled with a stream of nitrogen for 30 min then concentrated under reduced pressure. The residue is partitioned between 150 ml of water and 600 ml of methylene chloride (a solid formed at the interface). The aqueous layer (and solid) is extracted with additional methylene chloride (2×600 ml); the solid persisted in the aqueous layer. This is extracted with ethyl acetate (2×400 ml). The pooled methylene chloride extract is washed with saline, dried over magnesium sulfate and concentrated. The pooled ethyl acetate extract was dried over magnesium sulfate and concentrated. After crystallization from ethanol/water and recrystallization from ethanol an analytical sample had mp 188°–9°. The proposed structure is supported by NMR, IR and mass spectra as 4-(benzyloxy)indole-2-carboxamide.

4-(benzyloxy)indole-2-carboxamide (4.98 g) in 300 ml of methanol is stirred under 1 atm of hydrogen with 0.75 g of 10% palladium on carbon for 16 hr. The catalyst is filtered off through Celite filter aid, the filtrate concentrated, the residue taken up in ethyl acetate (300 ml) and filtered again. The clear filtrate is concentrated to 200 ml and hexane added to a volume of 450 ml. The cooled solution gives a small amount of gummy, dark material. The filtrate is diluted with hexane and cooled overnight to give a solid. Recrystallization from ethyl acetate/hexane then ethyl acetate gives 4-hydroxyindole-2-carboxamide, mp 219-221.

The 4-hydroxyindole-2-carboxanide ( 1.0 g), 1-chloro-3-[4-(diphenylmethyl)-1-piperinylpropane (2.4 g) and powdered potassium carbonate (0.9 g) are combined in acetone and heated at reflux overnight. The mixture is concentrated under reduced pressure, the residue is treated with ice water and the whole extracted with methylene chloride (3×300 ml). The pooled extract is washed with water, dried over magnesium sulfate and concentrated. The residue is triturated with methylene chloride and recrystallized from methanol-ethyl acetate to give the title compound, mp 222°-3°; structure is supported by NMR, IR and mass spectra.

EXAMPLE 6

4-[3-[4-[2,4-Dipyrrolidino-6-pyrimidinyl]-1-piperazinyl]propoxy]indole-2-carboxamide (VI)

4-(3-Chloropropoxy)indole-2-carboxamide (0.44 g), 4-(1-piperazinyl)-2,6-di-1-pyrrolidinylpyrimidine (0.525 g), powdered potassium carbonate (0.12 g) and sodium iodide (0.075 g) are combined in acetonitrile (50 ml) and heated at reflux for 96 hr. Although TLC showed both starting material and product remained in the reaction mixture, the mixture was concentrated under reduced pressure and the residue partitioned between 1N potassium bicarbonate and methylene chloride. The layers are separated, the aqueous layer is extracted with methylene chloride, the pooled organic extract is washed with water, then saline, dried over magnesium sulfate and concentrated. The residue is chromatographed over silica gel (250 ml) and eluted with methanol/methylene chloride (3.5/96.5). The appropriate fractions are pooled and concentrated. Crystallization from acetonitrile gives the title compound, mp 151°-2° (foam); the proposed structure is supported by NMR, IR and mass spectra.

EXAMPLE 7

2-Cyano4-[3-[4-(diphenylmethyl)-1-piperazinyl]-propoxy]indole, dihydrochloride (VI)

4-[3-[4-(Diphenylmethyl)-1-piperazinyl]propoxy]indole-2-carboxamide (EXAMPLE 5, 1.45 g) and pyridine (1.18 ml) in dioxane (442) ml) is cooled to 12°. Trifluoroacetic anhydride (1.1 ml) in dioxane (8 ml) is added dropwise over 15 min (the reaction temperature remained between 12° and 14° ). The mixture is stirred for 2 hr at 20°-25°, diluted with methylene chloride and the mixture is washed with aqueous sodium bicarbonate, water and finally saline. The organic solution is dried over magnesium sulfate and concentrated to give a solid. The residue is dissolved in ether, filtered through magnesol, and the solution concentrated to give the free base of the title compound. The hydrochloride salt is prepared and recrystallized with an impurity. The solids and filtrates are combined, concentrated, and the residue partitioned between saturated sodium bicarbonate and methylene chloride to give the free base. This is chromatographed over silica gel (500 ml), eluting with methanol/methylene chloride (2.5/97.5). Twenty ml fractions are collected. Fractions 58-84 contained clean product. The hydrochloride salt is prepared from an ether solution by the addition of ethereal hydrochloric acid. Recrystallization from methanol/acetone/ether gives the title compound, mp 231°-2°. The proposed structure is supported by NMR, IR and mass spectra.

EXAMPLE 8

2-Cyano4-[3-[4-(2,4-dipyrrolidino-6-pyrimidinyl)-1-piperazinyl]propoxy]indole (VI)

The 4-hydroxyindole-2-carboxamide (EXAMPLE 5, 0.44 g), 4-(1-piperazinyl)-2,6-di-1-pyrrolidinylpyrimidine (0.525 g, 1.74 mmol), powdered potassium carbonate (0.12 g, 0.87 mmol) and sodium iodide (0.075 g) are combined in acetonitrile (50 ml) and heated at reflux for 96 hr. Although TLC showed starting material remained in the reaction mixture, the mixture is concentrated under reduced pressure and the residue partitioned between 1N potassium bicarbonate and methylene chloride. The layers are separated, the aqueous layer is extracted with methylene chloride. The pooled organic extract is washed with water, then saline, dried over magnesium sulfate and concentrated. The residue is chromatographed over silica gel (250 ml) and eluted with methanol/methylene chloride (3.5/96.5). The appropriate fractions are pooled and concentrated; crystallization from acetonitrile gives 4-[3-[4-[2,4-dipyrrolidino-6pyrimidinyl]-1-piperazinyl]propoxy]indole-2-carboxamide, mp 151°-2° (foam). The proposed structure is supported by NMR, IR and mass spectra.

A solution of 4-[3-[4-[2,4-dipyrrolidino-6-pyrimidinyl]-1-piperazinyl]propoxy]indole-2-carboxamide (0.45 g) in dioxane (12 ml), under nitrogen, is mixed with pyridine (0.33 ml), cooled to 12° and treated during 5 min. with a solution of trifluoroacetic anhydride (0.31 ml) in dioxane (2.5 ml). The mixture is stirred at 12° for 15 min. and at 20°-25° for 18 hr. It is again cooled to 12° and treated with additional trifluoroacetic anhydride (0.1 ml) in dioxane (1 ml). The mixture is kept at 12° for 15 min. and at 20°-25° for 4 hr. It is then diluted with methylene chloride; washed with saturated sodium bicarbonate, water and saline, dried over magnesium sulfate and concentrated under reduced pressure. The residue is chromatographed over silica gel (275 ml) with eluting with ammonium hydroxide/methanol/methylene chloride (0.5/5/94.5). The product isolated from this column is crystallized from methanol to give the title compound, mp of an analytical sample 147°-149°;, Anal. calc'd for $C_{28}H_{36}N_8O$: C, 67.17; H, 7.25; N, 22.38. Found: C, 66.80; H, 7.34; N, 21.78.

CHART A
SENSITIZING AMINES
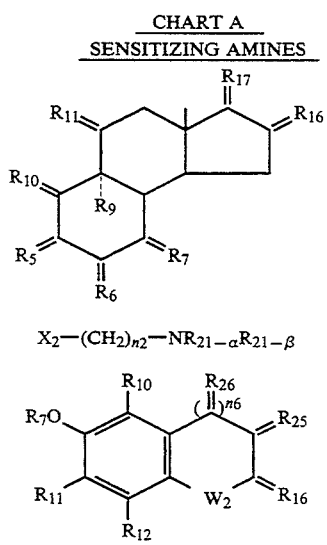 (I)
$X_2-(CH_2)_{n2}-NR_{21-\alpha}R_{21-\beta}$ (II)
(III)
(IV)
(V)
(VI)
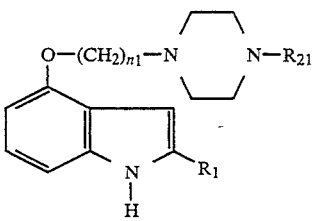
CHART B
| | |
|---|---|
| pyridine-2-, | (F-1) |
| 3-, | (F-2) |
| or 4-yl optionally substituted optionally as the N-oxide | (F-3) |
| $-{}^*CH_2-(CH_2)_c-G-(CH_2)_d-CH_2-N^*-$ | (F-4) |
| 3-pyrrolin-1-yl | 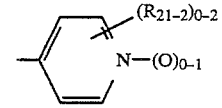 (F-5) |
| pyrrol-1-yl optionally substituted | 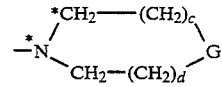 (F-6) |
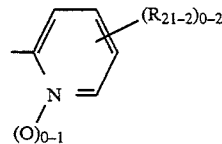
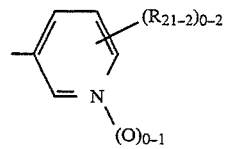
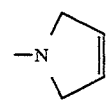
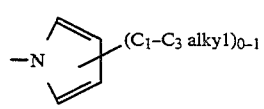

CHART B-continued

| | | |
|---|---|---|
| piperidin-1-yl optionally substituted | 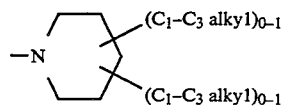 | (F-7) |
| 1,2,3,6-tetrahydropyridin-1-yl | 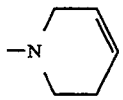 | (F-8) |
| 1-hexamethyleneimino containing a 3- or 4- double bond or 3- and 5- double bonds | 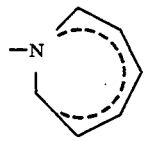 | (F-9) |
| 1,4-dihydro-1-pyridinyl substituted in the 4-position | 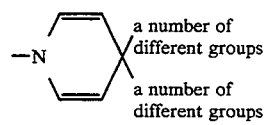 a number of different groups / a number of different groups | (F10) |
| 1,3,5-triazin-2-yl or the $N_1$-oxide thereof optionally substituted at the 4- and/or 6- position | 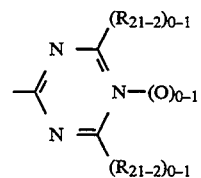 | (F-11) |
| pyrimidin-4-yl or the $N_1$-oxide thereof optionally substituted at the 2- and/or 6- and 5- and/or 6- position | 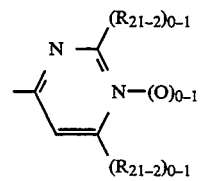 | (F-12) |
| pyrimidin-2-yl optionally substituted | 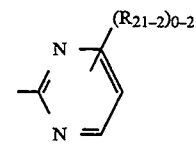 | (F-13) |
| pyrazin-2-yl optionally substituted | 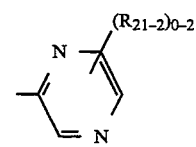 | (F-14) |
| imidazol-2-yl optionally substituted | 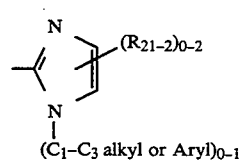 | (F-15) |
| 1,3,4-triazol-2-yl optionally substituted | 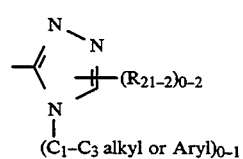 | (F-16) |
| imidazol-4- or 5-yl optionally substituted | 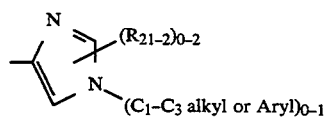 | (F-17) |

CHART B-continued benzo[b]thien-2-yl 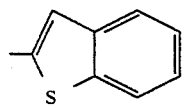 (F-18)

indol-2-yl 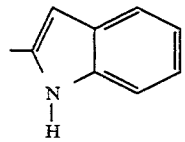 (F-19)

benzo[b]thiazol-2-yl 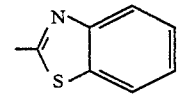 (F-20)

benzimidazol-2-yl 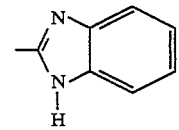 (F-21)

4-[2-[4-[2,6-di-(1-pyrrolidinyl)-4-pyrimidinyl]-1-piperazinyl]ethyl] 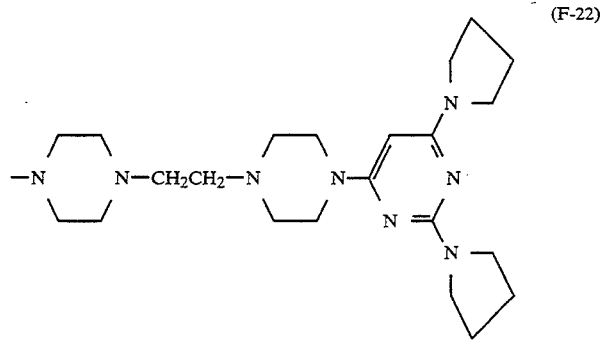 (F-22)

1,2,4-triazin-3-yl optionally substituted at the 5- and/or 6-position 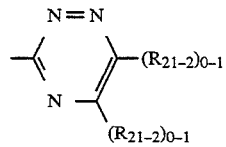 (F-23)

(1-piperazinyl)-($C_2$–$C_4$) optionally substituted in the 4-position 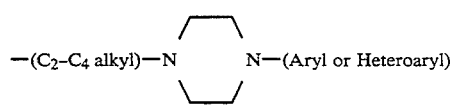 (F-24)

(1-piperazinyl)acetyl substituted in the 4-position 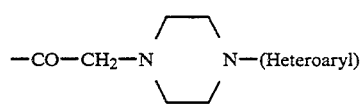 (F-25)

(1-piperazinyl)carbonylmethyl substituted in the 4-position 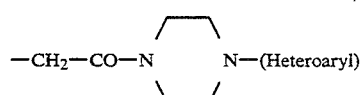 (F-26)

2-(carboxy)-1-pyrrolidinyl 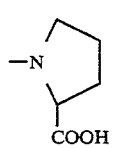 (F-27)

CHART B-continued 2-(carboxy)-1-piperidinyl 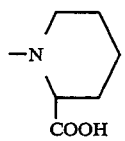 (F-28)

2-(carboxy)-1-hexamethyleneimino 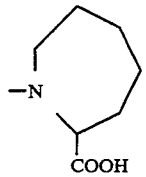 (F-29)

2-(carboxy)-1-heptamethyleneimino 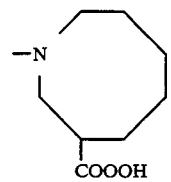 (F-30)

1-piperazinyl substituted
in the 4-position 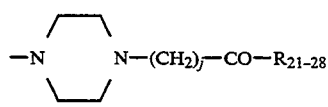 (F-31)

1-piperazinyl substituted in
the 4-position 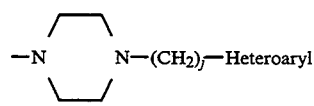 (F-32)

1-piperazinyl substituted
in the 4-position 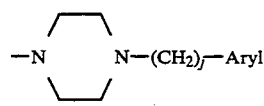 (F-33)

4-hydroxy-1-piperidinyl
substituted in the
4-position 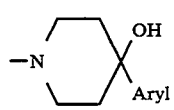 (F-34)

1-piperazinyl
substituted in
the 4-position 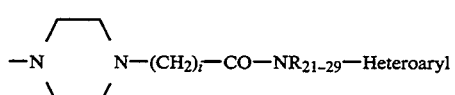 (F-35)

1-piperazinyl substituted
in the 4-position 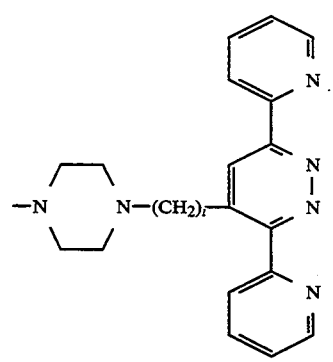 (F-36)

CHART B-continued
| | |
|---|---|
| 1-piperazinyl substituted in the 4-position | (F-37) 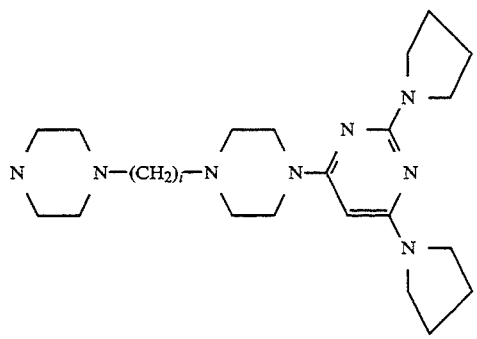 |
We claim:
1. A indole which is selected from the group consisting of
   4-[3-[4-(diphenylmethyl)-1-piperazinyl ]propoxy]indole-2-carboxamide,
   4-[3-[4-[2,4-dipyrrolidino-6-pyrimidinyl]-1-piperazinyl]propoxy]indol-2-carboxamide.
* * * * *